(12) United States Patent
Levin et al.

(10) Patent No.: US 11,427,530 B2
(45) Date of Patent: Aug. 30, 2022

(54) SYNTHESIS OF 4-CHLOROKYNURENINES AND INTERMEDIATES

(71) Applicant: VISTAGEN THERAPEUTICS, INC., South San Francisco, CA (US)

(72) Inventors: Daniel Levin, La Canada (CA); Peter Leeming, Monrovi, CA (US); Emerich Eisenreich, Claremont, CA (US); Xuejun Karl Liu, Arcadia, CA (US)

(73) Assignee: VISTAGEN THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 16/967,627

(22) PCT Filed: Feb. 11, 2019

(86) PCT No.: PCT/US2019/017448
§ 371 (c)(1),
(2) Date: Aug. 5, 2020

(87) PCT Pub. No.: WO2019/157426
PCT Pub. Date: Aug. 15, 2019

(65) Prior Publication Data
US 2021/0276942 A1 Sep. 9, 2021

Related U.S. Application Data

(60) Provisional application No. 62/628,580, filed on Feb. 9, 2018.

(51) Int. Cl.
| | | |
|---|---|---|
| *C07C 227/18* | (2006.01) | |
| *C07C 227/16* | (2006.01) | |
| *C07C 227/20* | (2006.01) | |
| *C07C 227/32* | (2006.01) | |
| *C07C 227/40* | (2006.01) | |
| *C07C 229/36* | (2006.01) | |
| *C07C 229/42* | (2006.01) | |
| *C07C 269/06* | (2006.01) | |
| *C07C 271/22* | (2006.01) | |
| *C07C 303/28* | (2006.01) | |
| *C07F 3/06* | (2006.01) | |

(52) U.S. Cl.
CPC .......... *C07C 227/18* (2013.01); *C07C 227/16* (2013.01); *C07C 227/20* (2013.01); *C07C 227/32* (2013.01); *C07C 227/40* (2013.01); *C07C 229/36* (2013.01); *C07C 229/42* (2013.01); *C07C 269/06* (2013.01); *C07C 271/22* (2013.01); *C07C 303/28* (2013.01); *C07F 3/06* (2013.01)

(58) Field of Classification Search
None
See application file for complete search history.

(56) References Cited

U.S. PATENT DOCUMENTS

| | | | |
|---|---|---|---|
| 5,547,991 A | 8/1996 | Palfreyman | |
| 6,207,709 B1 | 3/2001 | Varasi | |
| 9,834,801 B2 | 12/2017 | Abele | |
| 2003/0130349 A1* | 7/2003 | Lobl | C07D 295/192 514/563 |
| 2016/0031800 A1 | 2/2016 | Tretyakov | |
| 2018/0327351 A1 | 11/2018 | Laufer | |

FOREIGN PATENT DOCUMENTS

| | | | |
|---|---|---|---|
| CN | 107129444 | * | 9/2017 |
| EP | 0501378 A1 | | 2/1992 |
| WO | 2014152752 A1 | | 9/2014 |
| WO | 2017/044516 A1 | | 3/2017 |
| WO | WO-2017065899 A1 * | 4/2017 | .......... C07B 59/001 |

OTHER PUBLICATIONS

National Center for Biotechnology Information (2021). PubChem Compound Summary for CID 126673236, NC1=C(C=CC(=C1)Cl)C(CC(C(=O)OC)NC(=O)OC(C)(C)C)=O. Retrieved Aug. 26, 2021 from https://pubchem.ncbi.nlm.nih.gov/compound/126673236, created on Apr. 22, 2017 (Year: 2017).*
Gao ("Palladium-Catalyzed Carbonylation of o-Iodoanilines for Synthesis of Isatoic Anhydrides" J. Org. Chem. Soc., 2014, 79, p. 4196-4200) (Year: 2014).*
Pubchem, Compound Summary for SID 333705743, Available Date: Apr. 22, 2017 (retrieved on Mar. 14, 2019). Retrieved from the Internet: <URL: https://pubchem.ncbi.nlm.nih.gov/substance/333705743> entire document.
Dunn et al., "Preparation of a Serine-Derived Organozinc Reagent in Tetrahydrofuran: Synthesis of Novel, Enantiomerically Pure Allenic, Acetylenic and Heteroaryl Amino Acids", Jul. 1993, SYNLETT, pp. 499-500.
Jackson et al., "Carbonylative coupling of organozinc reagents in the presence and absence of aryl iodides: synthesis of unsymmetrical and symmetrical ketones", J. Chem. Soc., Perkin Trans. 1, 1997, pp. 865-870.
Francesco G. Salituro et al.,"Enzyme-Activated Antagonists of the Strychnine-Insensitive Glycine/NMDA Receptor", Journal of Medicinal Chemistry, vol. 37, No. 3, (1994), pp. 334-336.
Nakamura Yoshitaka et al., "Catalytic, Asymmetric Mannich-Type Reactions of [alpha]-Imino Esters Bearing Readily Removable Substituents on Nitogen", Organic Letters, vol. 5, No. 14, (2003), pp. 2481-2484.

* cited by examiner

*Primary Examiner* — Amy C Bonaparte
(74) *Attorney, Agent, or Firm* — J.A. Lindeman & Co. PLLC

(57) ABSTRACT

The invention relates to an overall enantio-specific synthesis of 4-chlorokynurenine compounds, in particular L-4-chlorokynurenine, with improved yields. Large-scale syntheses are disclosed. The invention also relates to novel intermediates in the synthesis of L-4-chlorokynurenine.

12 Claims, No Drawings

SYNTHESIS OF 4-CHLOROKYNURENINES AND INTERMEDIATES

CROSS-REFERENCE TO RELATED APPLICATIONS

This application claims priority to U.S. Application No. 62/628,580 filed 9 Feb. 2018; the disclosure of which is incorporated herein by reference.

FIELD OF THE INVENTION

The invention relates to the enantiocontrolled synthesis of 4-chlorokynerenine compounds, and specifically of L-4-chlorokynurenine. The synthesis method yields L-4-chlorokynurenine in commercial quantities and is scalable for commercial manufacture. The invention also relates to certain chemical intermeditates in the syntheses of the invention.

BACKGROUND OF THE INVENTION

Kynurenic acid is a metabolically related brain constituent with anticonvulsant and neuroprotective properties (Stone, T. W.; *Pharmacal. Rev.* 1993, 45, 309-379). The biological activities of various derivatives of kynurenic acid and their kynurenine precursors have been studied (Camacho, E. et al. *J. Med. Chern.* 2002, 45, 263-274; Varasi, M. et al. *Eur. J. Med. Chern.* 1996, 31, 11-21; Salituro, F. G. et al. *J. Med. Chern.* 1994, 37, 334-336). Kynurenine compounds are converted to kynurenic acids in vivo. U.S. Pat. No. 5,547,991 describes methods of making 4,6-disubstituted tryptophan derivatives and their use as N-methyl-D-aspartate (NMDA) antagonists.

The lab-scale synthesis of L-kynurenine via a palladium (0) catalyzed reaction of an iodoalanine-derived organo zinc reagent with an aryl iodide under a carbon monoxide atmosphere has been reported by Jackson, et al., *J. Chem Soc., Perkin Trans.* 1, 1997, 865. While the experimental procedures reported by Jackson, et al., do provide L-kynurenine at the lab scale, there are issues and limitations rendering the procedures unsuitable for direct use in pharmaceutical grade manufacturing. For example, the procedures exhibit poor selectivity with regard to by-products such that costly, low-loading preparative chromatography is needed to achieve acceptable product purity. Poor control in respect of temperature and exotherm make the procedure unsuitable and unsafe for scale-up. This synthesis demonstrated deteriorating efficiency (yield) with some substituted iodo-aryls and other unaddressed scale limiting factors exist such as gas mass transport across the gas/liquid interface. The reaction conditions described have low static CO pressure with a very large surface area to volume ratio for the reaction mixture in order to achieve necessary CO gas mass transfer efficiency to enable a sufficient CO dissolution rate and concentration of CO in the reaction mixture for the carbonylation reaction which limits scale up efficiency. Such issues and deficiencies render the lab-scale synthesis described therein unsuitable for direct use at commercial scale and for economic high quality pharmaceutical active ingredient manufacturing.

L-4-chlorokynurenine is a prodrug of L-7-chlorokynurenic acid and L-4-chlorokynurenine readily gains access to the central nervous system (CNS) after administration. L-4-chlorokynurenine, presumably a zwitterion at physiological pH, is efficiently converted to L-7-chlorokynurenic acid within activated astrocytes, and, after dosing with L-4-chlorokynurenine, brain levels of L-7-chlorokynurenic acid are increased at sites of neuronal injury or excitotoxic insult as a result of astrocyte activation. In preclinical studies, L-4-chlorokynurenine has shown anti-seizure activity in rats. The compound also was found to increase the firing rate and burst firing activity of dopaminergic neurons in the brains of rats. See published PCT applications WO 2014/116739 A1 and WO 2016/191352 A1 as well as the references cited therein. Given the beneficial pharmacological properties and efficicay of L-4-chlorokynurenine, there is a need for manufacturing processes pharmaceutical quality L-4-chlorokynurenine on a large commercial scale.

An enantioselective synthesis of L-4-chlorokynurenine described by Salituro et al. was used for the synthesis of gram quantities of L-4-chlorokynurenine (Salituro, F. G. et al. *J. Med. Chern.* 1994, 37, 334-336). This synthesis is not practical for scale up on a commercial manufacturing scale due to the use of hazardous and/or toxic reagents such as trimethyl tin chloride, sodium hydride, and tert-butyllithium and the poor availability of certain building blocks.

Methods for the synthesis of a class of 4,6-disubstituted kynurenines derivatives, including L-4-chlorokynurenine, and their use as antagonists to the NMDA receptor are described in U.S. Pat. No. 5,547,991. Pharmaceutical compositions containing these compounds, and their therapeutic use are also described.

A racemic synthesis of 4-chlorokynurenine was reported in Varasai et al., *Eur. J. Med. Chern.* 1996, 31, 11-21. However, experiments described therein for the separation of the enantiomers by crystallization of diastereomeric salts were not successful, nor was preparative high performance liquid chromatography (HPLC) described therein substantially successful, due to low solubility.

Two enantioselective synthetic routes to L-4-chlorokynurenine are disclosed in published PCT applications WO 2014/152752 and WO 2014/152835. WO 2014/152752 discloses the synthesis of L-4-chlorokynurenine from an aniline starting material. The synthesis of WO 2014/152835 uses an indole aldehyde starting material and proceeds through an oxidative ring-opening step.

There is a need for an improved synthesis L-4-chlorokynurenine that may be accomplished on a commercially relevant scale using commercially available reagents that does not require the use of toxic and/or hazardous reagents or costly and low-yielding purification techniques. There is a need for synthesis suitable for large scale manufacture and that can produce chlorokynurenine compounds, particularly L-4-chlorokynurenine, in high chemical purity and high chiral purity. There is a need for an efficient and robust synthesis of L-4-chlorokynurenine suitable for commercial manufacture of pharmaceutical quality materials meeting regulatory requirements while also being suitable for safe and robust operation at commercial manufacturing scale.

SUMMARY OF THE INVENTION

In one embodiment, the invention relates to an overall enantio-specific synthesis of 4-chlorokynurenine compounds (8), particularly L-4-chlorokynurenine (8a) as shown in Schemes I and II below. The invention relates to methods for their preparation with improved process conditions suitable for safe, efficient, and scaleable stereocontrolled manufacture. The methods of the invention overcome the limitations and shortcomings of previously reported syntheses.

The invention relates to a method for the enantio-specific preparation of 4-chlorokynurenine (8) according to Scheme I,

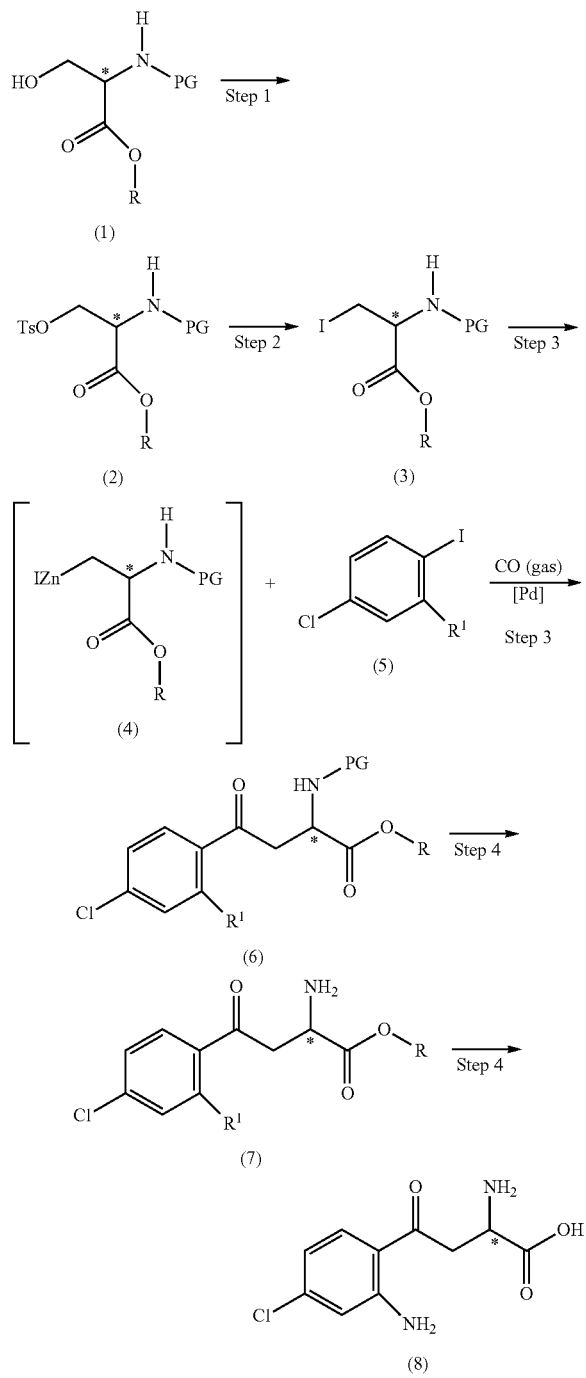

Scheme I, wherein R is a $C_1$-$C_{12}$ alkyl group, a $C_1$-$C_{12}$ alk-aryl group, an aryl group, or a heteroaryl group; * indicates an asymmetric carbon which may be a single enantiomer or a mixtures of enantiomers which is maintained throughout; PG is an amino protecting group; Ts is a tosyl group; $R^1$ is $NH_2$, NH(PG) or $NO_2$; and X is Cl, Br, I, triflate or tosylate. A method of the invention has the following steps:

Step 1, reacting a protected serine ester (1) with toluene-sulfonyl chloride under suitable reaction conditions to convert the protected serine ester to its corresponding tosylate (2), Step 2, reacting the tosylate (2) with sodium iodide or potassium iodide under an inert atmosphere in the absence of light under suitable reaction conditions to replace the tosyl group with iodide and form the corresponding iodo intermediate (3), Step 3, converting the iodo intermediate (3) in situ to a zinc reagent (4) in the absence of light under suitable reaction conditions and forming a protected ester compound (6) via a carbonylation reaction reacting the zinc reagent (4) with a compound (5) in the presence of a palladium (0) catalyst [Pd] under suitable reaction conditions and while maintaining a sustained dissolved CO concentration either by continuous subsurface CO addition and/or CO pressure, optionally purifying the protected ester compound (6), and Step 4, deprotecting the protected ester compound (6) in the absence of light under suitable reaction conditions to remove any protecting group PG, and, when $R^1$ is $NO_2$, reducing the $NO_2$ group to an $NH_2$ group, to form the ester (7), and deprotecting (hydrolyzing) the ester (7) in the absence of light without exposure to air under suitable reaction conditions to form 4-chlorokynurenine (8) after adjustment to an acidic pH, wherein the deprotecting and reducing reactions are done in a single step or in multiple steps.

The invention also relates to a method for the preparation of L-4-chlorokynurenine (8a) according to Scheme II,

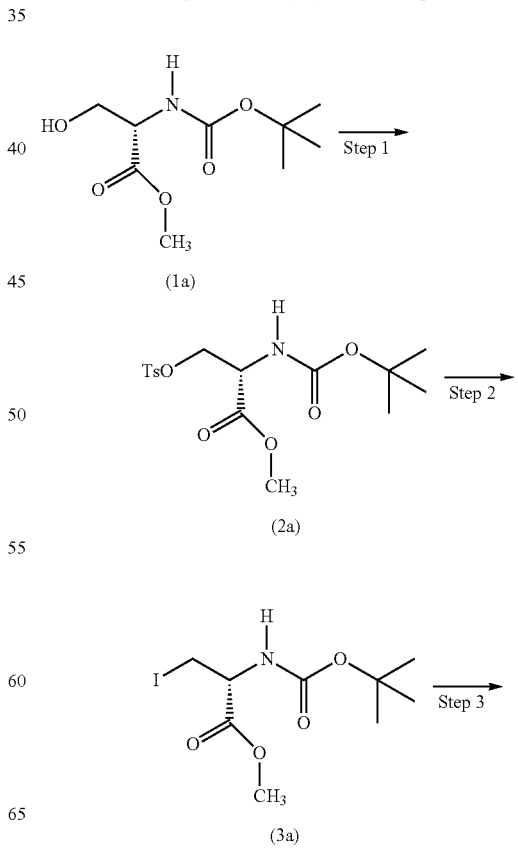

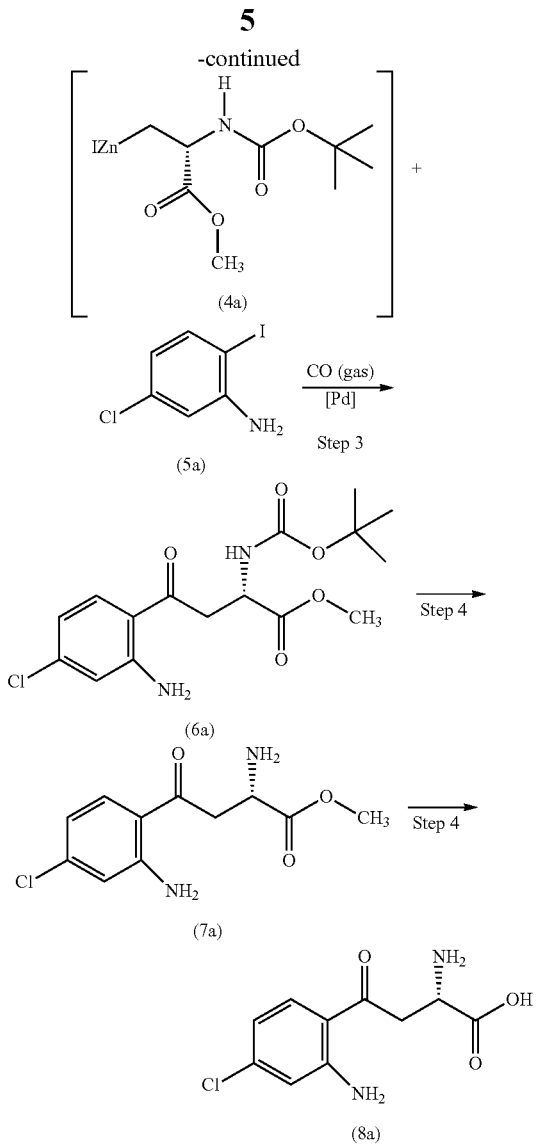

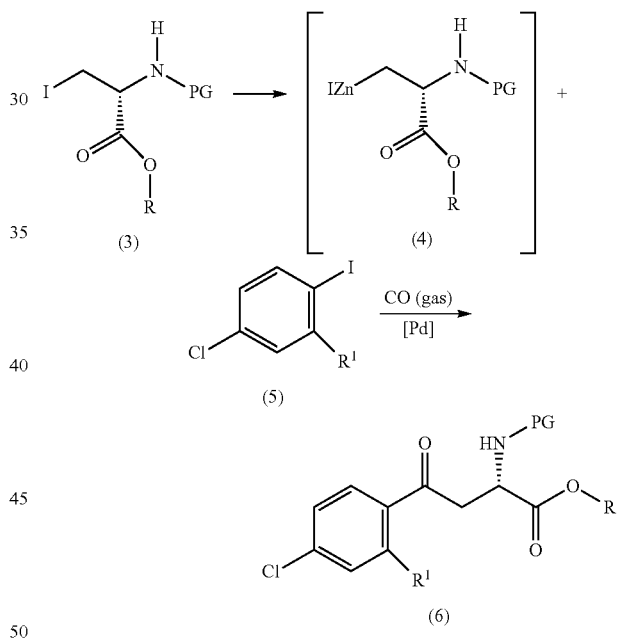

tions to remove the protecting group to form the methyl ester (7a) taking precautions to avoid exposing the isolated solids to air or moisture, and then deprotecting (hydrolyzing) the methyl ester (7a) in the absence of light without exposure to air under suitable reaction conditions to form 4-chlorokynurenine (8a) after adjustment to an acidic pH, wherein the deprotecting reactions are done in a single step or in two steps.

In other embodiments of the inventions the methods shown in Schemes I and II may also include the steps of:
as the pH adjustment, isolating the 4-chlorokynurenine (8)/L-4chlorokynurenine (8a) from alkaline solution as a fee acid with aqueous acid to a pH below 6.5,
dissolving the isolated free acid (8)/(8a) in aqueous acid at a pH below 2,
precipitating the free acid (8)/(8a) by adjusting the pH of 4.5 to 6.5,
collecting the precipitated free acid (8)/(8a),
drying the collected free acid (8)/(8a), and
optionally, triturating the collected free acid (8)/(8a) using an organic solvent or an organic solvent mixture and drying the triturated free acid (8)/(8a).

Another embodiment of the invention relates to a method of preparing a compound 6 from a compound 3

Scheme II, wherein Ts is a tosyl group. A method of the invention has the following steps of:

Step 1, reacting a BOC-L-serine methyl methyl ester (1a) with toluenesulfonyl chloride under suitable reaction conditions to convert the BOC-L-serine methyl ester (1a) to its corresponding tosylate (2a), Step 2, reacting the tosylate (2a) with sodium iodide or potassium iodide under an inert atmosphere in the absence of light under suitable reaction conditions to replace the tosyl group with iodide and form the corresponding iodo intermediate (3a), Step 3, converting the iodo intermediate (3a) in situ to a zinc reagent (4a) in the absence of light under suitable reaction conditions and forming a BOC-protected methyl ester compound (6a) via a carbonylation reaction and reacting the zinc reagent (4a) with a 5-chloro-iodo aniline compound (5a) in the presence of a palladium (0) catalyst [Pd] and while maintaining a sustained dissolved CO concentration either by continuous subsurface CO addition and/or CO pressure,
optionally purifying the protected ester compound (6a), and Step 4, deprotecting the BOC protected ester compound (6a) in the absence of light under suitable reaction conditions wherein R is a $C_1$-$C_{12}$ alkyl group, a $C_1$-$C_{12}$ alk-aryl group, an aryl group, or a heteroaryl group; * indicates an asymmetric carbon which may be a single enantiomer or a mixtures of enantiomers which is maintained throughout; PG is an amino protecting group; Ts is a tosyl group; $R^1$ is $NH_2$, NH(PG) or $NO_2$; and X is Cl, Br, I, triflate or tosylate. The method has the following steps: converting the iodo intermediate (3) in situ to a zinc reagent (4) in the absence of light under suitable reaction conditions and forming a protected ester compound (6) via a carbonylation reaction reacting the zinc reagent (4) with a compound (5) in the presence of a palladium (0) catalyst [Pd] under suitable reaction conditions and while maintaining a sustained dissolved CO concentration either by continuous subsurface CO addition and/or CO pressure, and optionally purifying the protected ester compound (6).

Another embodiment of the invention relates to a method of preparing a compound 6a from a compound 3a

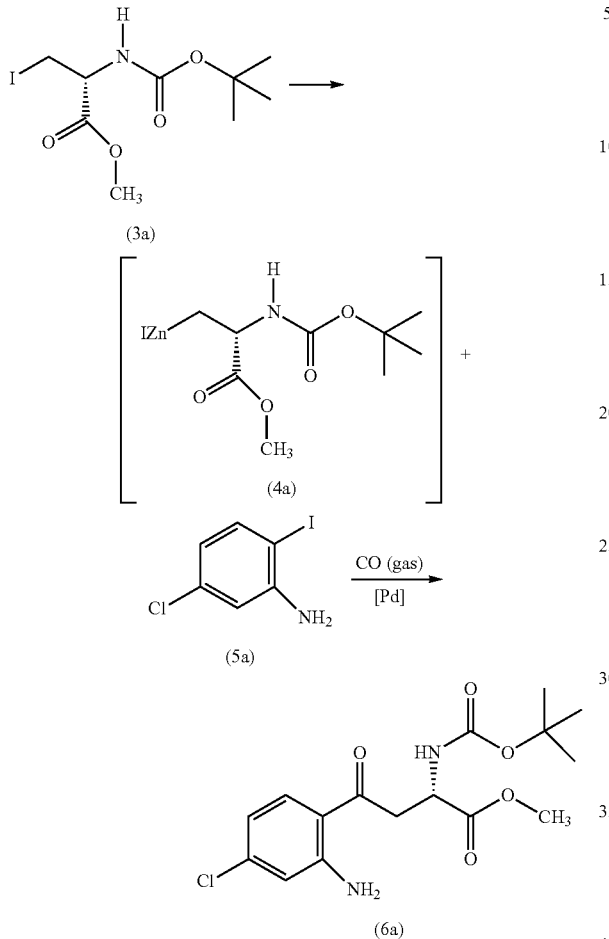

(3a)

(4a)

(5a)

(6a)

comprising the steps of converting the iodo intermediate (3a) in situ to a zinc reagent (4a) in the absence of light under suitable reaction conditions and forming a BOC-protected methyl ester compound (6a) via a carbonylation reaction and reacting the zinc reagent (4a) with a 5-chloro-iodo aniline compound (5a) in the presence of a palladium (0) catalyst [Pd] and while maintaining a sustained dissolved CO concentration either by continuous subsurface CO addition and/or CO pressure, optionally purifying the protected ester compound (6a).

In another embodiment, the invention relates to a synthetic intermediate of formula 6a:

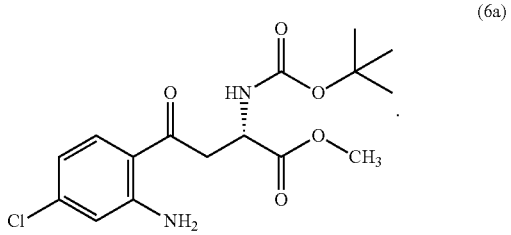 [SMILES: COC(=O)[C@H](CC(=O)c1ccc(Cl)cc1N)NC(=O)OC(C)(C)C]

(6a)

In another embodiment, the invention relates to a synthetic intermediate of formula 7a:

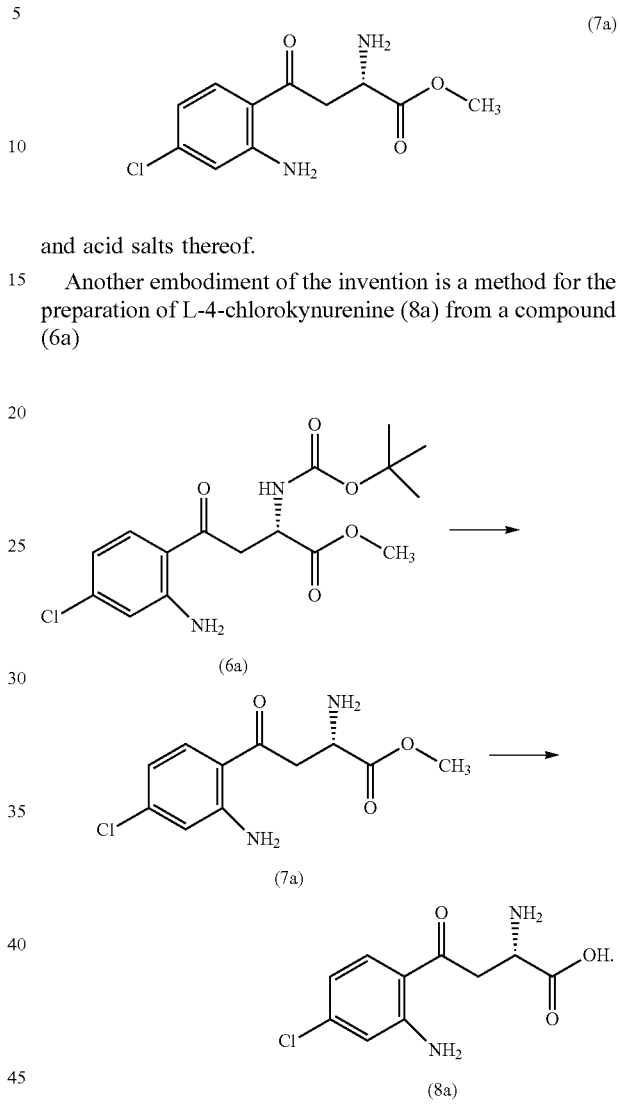

(7a)

and acid salts thereof.

Another embodiment of the invention is a method for the preparation of L-4-chlorokynurenine (8a) from a compound (6a)

(6a)

(7a)

(8a)

The method deprotects the BOC protected ester compound (6a) in the absence of light under suitable reaction conditions to remove the protecting group to form the methyl ester (7a) taking precautions to avoid exposing the isolated solids to air or moisture, and then deprotecting (hydrolyzing) the methyl ester (7a) in the absence of light without exposure to air under suitable reaction conditions to form 4-chlorokynurenine (8a) after adjustment to an acidic pH The deprotecting reactions are done in a single step or in two steps.

DESCRIPTION OF THE INVENTION

The invention relates to the enantio-specific synthesis of 4-chlorokynurenine compounds (8), such as L-4-chlorokynurenine (8a), (which also is referred to by the chemical name (S)-2-amino-4-(2-amino-4-chlorophenyl)-4-oxobutanoic acid), both shown below.

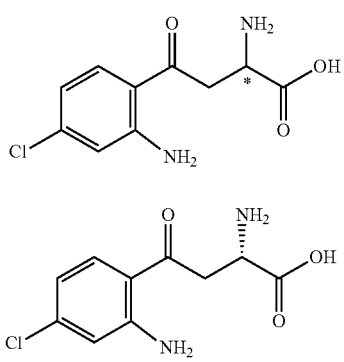

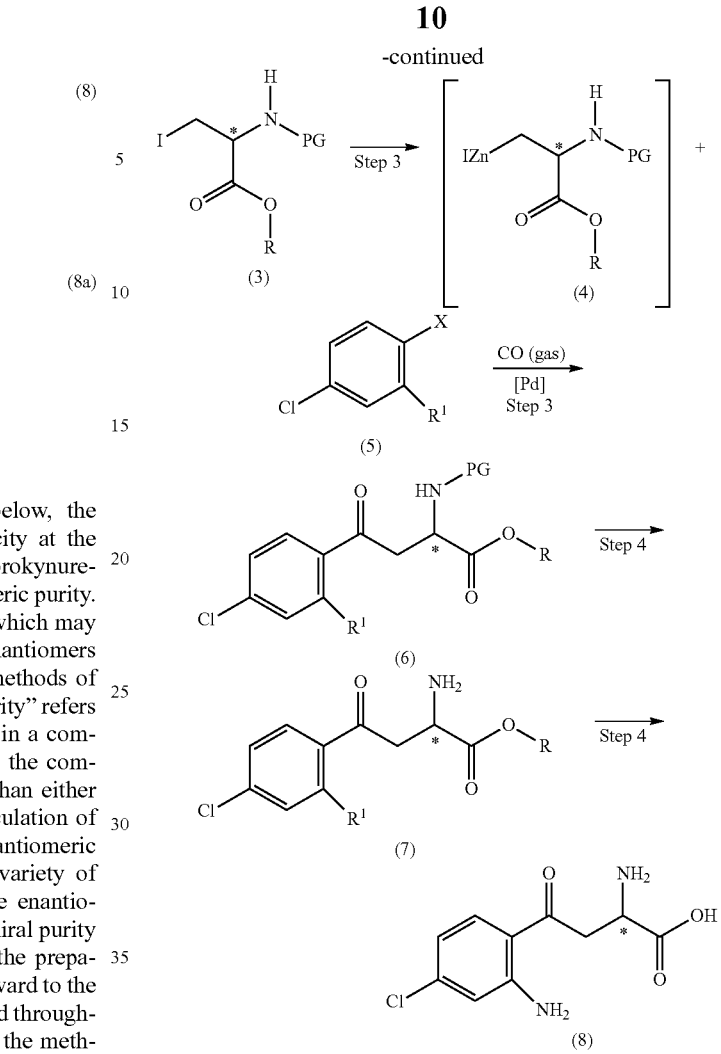

As shown in Schemes I and II repeated below, the methods of the invention retain enantio-specificity at the 2-position throughout the preparation of a 4-chlorokynurenine and yield products possessing high enantiomeric purity. The asterisk (*) indicates an asymmetric carbon which may be a single enantiomer (D or L) or a mixtures of enantiomers (D and L) which is maintained throughout the methods of the invention. "Enantiomeric purity" or "chiral purity" refers to the overall level of one particular enantiomer in a composition as compared to the other enantiomer in the composition. Components of the composition other than either of the enantiomers are not considered in the calculation of "enantiomeric purity" or "chiral purity." The enantiomeric purity or chiral purity may be measured by a variety of techniques, including chiral HPLC analysis. The enantio-specificity and chiral purity is controlled by the chiral purity of the starting material (1)/(1a) that is used for the preparation of compound (3)/(3a) and subsequently forward to the final product (8)/(8a). The chiral center is preserved throughout the synthesis. For L-4-chlorokynurenine (8a) the methods of the invention achieve a chiral purity of ≤5% of the undesired D-isomer.

Scheme I below depicts a general overall enantio-specific preparation of 4-chlorokynurenine compounds (8) according to the invention.

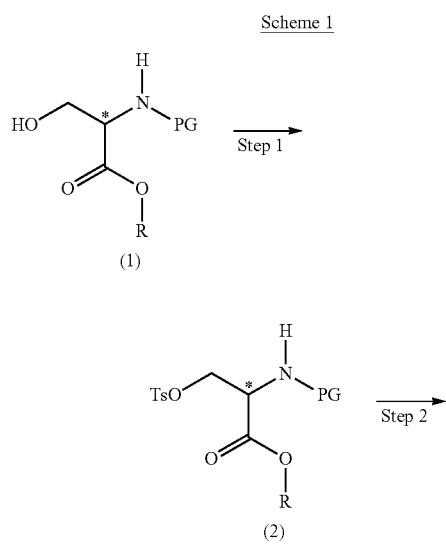

In Scheme I, the group R is a $C_1$-$C_{12}$ alkyl group, a $C_1$-$C_{12}$ alk-aryl group, an aryl group or a heteroaryl group. An alkyl group or the alkyl portion of an alk-aryl group may be linear or branched. The alkyl or alkyl portion of an alk-aryl groups is a $C_1$-$C_{12}$ alkyl, preferably a $C_1$-$C_6$ alkyl. For example, R may be methyl, ethyl, propyl, isopropyl, butyl, t-butyl, pentyl, isopentyl, hexyl, isohexyl, heptyl, octyl, nonyl, decyl, undecyl, dodecyl and branched variations of each above alkyl. When R is a $C_1$-$C_{12}$ alkyl group, it is most preferably methyl or ethyl. When R is a $C_1$-$C_{12}$ alk-aryl group, a $C_1$-$C_{12}$ alkyl group (or one of the preferred alkyl groups just discussed) is bonded to aryl group such as phenyl, naphthyl and the like. A $C_1$-$C_{12}$ alk-aryl group may be for example, benzyl ($CH_2C_6H_5$), ethylphenyl ($CH_2CH_2C_6H_5$), methylnapthyl ($CH_2C_{10}H_9$), etc. Suitable aryl groups for R include but are not limited to phenyl, napthyl, and the like. Suitable heteroaryl groups for R include but are not limited to furyl, thienyl, pyridyl, and the like.

Any amine protecting group, PG, known in the art may be used. Suitable amine protecting groups include, but are not limited to acetyl (Ac), t-butyloxycarbonyl (BOC), 9-fluoroenyl methyloxycarbonyl (Fmoc), benzyl, benzoyl, carboxybenzyl (CBz), p-methoxybenzyl carbonyl (MOZ), and the like. See, e.g., isidro-Liobet, et. Al. Chem Rev., 2009, 109 (6), 2455-2504. Preferred protecting groups include BOC and Fmoc.

The group Ts on compound (2) is a tosyl group, $CH_3C_6H_4SO_2$.

The group X is a leaving group such as, but not limited to, Cl, Br, I, triflate or tosylate. Other leaving groups known in the art may be used. A preferred leaving group is I.

In a preferred method of the invention according to Scheme I, R is a $C_1$-$C_6$ alkyl group; PG is an amine protecting group selected from BOC, Fmoc, Benzyl, Benzoyl, alkylamine, arylamine, TFA, and CBz; and X is I. In another, R is a methyl group, PG is the amino protecting group BOC, and X is I.

Scheme II depicts a particular method of the invention, the overall synthesis of L-4-chlorokynurenine (8a) according to the invention. The synthesis of Scheme II is a preferred synthesis of Scheme I.

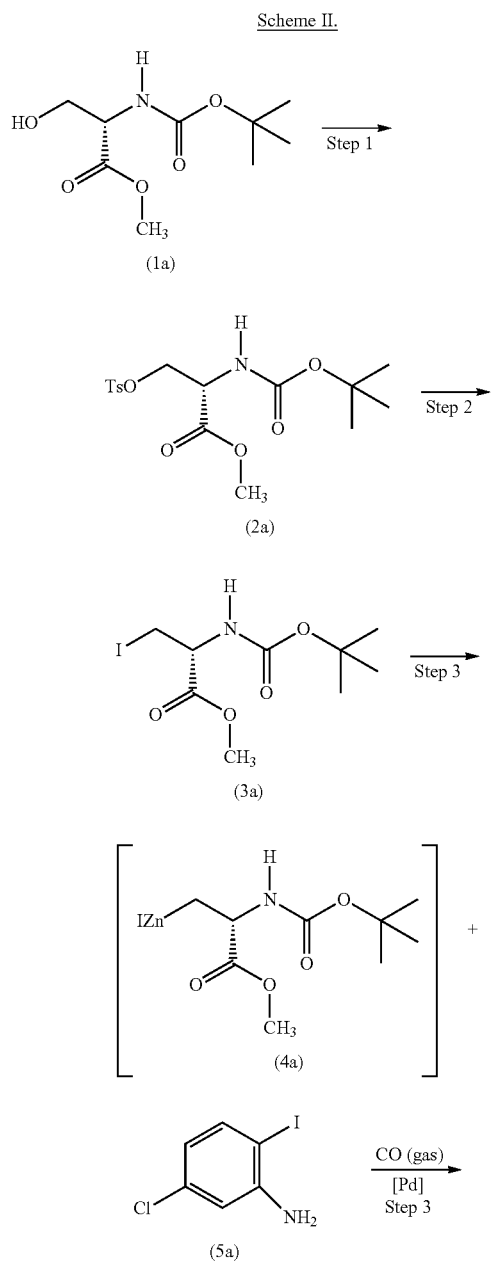

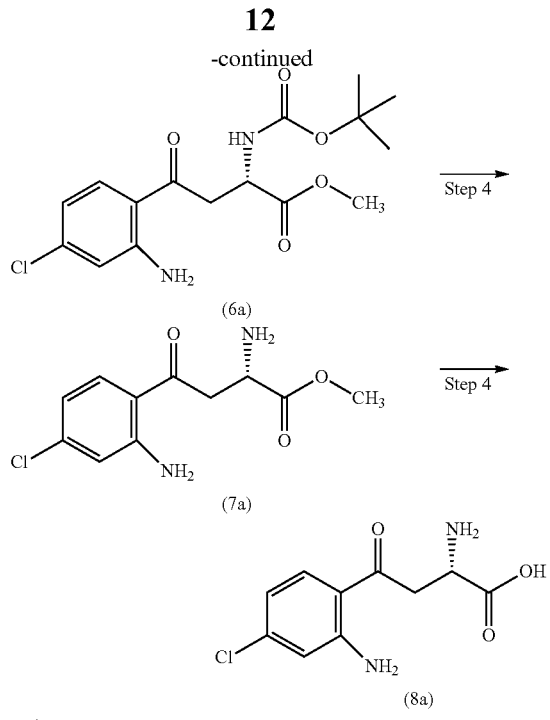

Ts is tosyl.

In general, a method of preparing 4-chlorokynurenines according to the invention, such as shown in Schemes I and II, proceeds along the following synthtic path. In Step 1, a protected serine ester (1), e.g. BOC-L-serine methyl methyl ester (1a), is first converted to its corresponding tosylate (2)/(2a). In Step 2, the tosyl group is replaced with iodide to form the iodo intermediate (3)/(3a). The iodo group of intermediate (3)/(3a) is converted in situ to an iodo-zinc reagent (4)/(4a) as step 3 which is then (as part of the same step) coupled to a 5-chloroaniline compound (5) having leaving group X, e.g., 5-chloro-2-iodoaniline (5a) using carbon monoxide and a palladium (0) catalyst [Pd] to form a protected ester intermediate (6), e.g. a BOC-protected, methyl ester intermediate (6a) which is a fully protected form of L-4-chlorokynurenine (8a). The protected ester intermediate (6) may be purified prior to the next steps in the synthesis of Scheme I or of Scheme II. Deprotection occurs in Step 4 to convert intermediate (6) to an ester of L-4-chlorokynurenine (7), e.g. the methyl ester of L-4-chlorokynurenine (7a) and then conversion of the ester (7) to the acid form of L-4-chlorokynurenine (8), e.g. L-4-chlorokynurenine (8a) after adjustment to an acidic pH. The deprotecting steps in step 4 may be sequential or performed in parallel using reaction conditions appropriate for the particular protecting group used as is known in the art.

One embodiment of the invention is a method for the preparation of 4-chlorokynurenine compounds (8) according to Scheme I. Another embodiment of the invention are methods that prepare 4-chlorokynurenine (8) according to Scheme I using Steps 1-4 described below. The Examples below describe additional steps and preferred embodiments of the methods of the invention.

Step 1 of Scheme I reacts a protected serine ester (1) with toluenesulfonyl chloride under suitable reaction conditions to convert the protected serine ester to its corresponding tosylate (2). In a preferred embodiment, 1 to 2 molar equivalents of toluenesulfonyl chloride may be used at a reaction temperature ranging from −50° to 50° C., −40° to 40° C., -30° to 30° C., -20° to 20° C., -10° to 10° C., preferably -5° to 5° C. In a further preferred embodiment, Step 1 is carried out in the presence of a catalytic amount of 4-dimethylaminopyridine and, optionally, includes isolating and recrystallizing the tosylate (2).

Step 2 of Scheme I reacts the tosylate (2) with sodium iodide or potassium iodide, preferably sodium iodide, under an inert atmosphere in the absence of light under suitable reaction conditions to replace the tosyl group with iodide and form the corresponding iodo intermediate (3). In a preferred embodiment, the reaction temperature may range from -20° to 60° C., -10° to 50° C., 0° to 40° C., more preferably 10° to 30° C. In a further preferred embodiment, Step 2 includes an aqueous quench of the reaction mixture into water at a temperature ranging from 0° to 40° C., 0° to 30° C., 0° to 20° C., and more preferably 0° to 10° C., to precipitate the iodo intermediate (3) and, optionally, recrystallization of the iodo intermediate (3).

Step 3 of Scheme I converts the iodo intermediate (3) in situ to a zinc reagent (4) in the absence of light under suitable reaction conditions and forming a protected ester compound (6) via a carbonylation reaction reacting the zinc reagent (4) with a compound (5) in the presence of a palladium (0) catalyst [Pd] under suitable reaction conditions and while maintaining a sustained dissolved CO concentration either by continuous subsurface CO addition and/or CO pressure. In a preferred embodiment, the reaction temperature may range from 0° to 50° C., 10° to 40° C., 15° to 35° C., more preferably 20° to 30° C. Pallidium (0) catalysts used for coupling reactions may be used. See, e.g., Colacot, Platinum Metals Rev., 2012, 56, (2), 110-116. Ligands for Pd(0) catalysts include for example dppm, dppe, dppp, dcpe, PPh$_3$, P(cyclohexyl)$_3$, P(t-Bu)$_3$, P(C$_6$F$_5$)$_3$, P(2, 4,6-MeC$_6$H$_2$)$_3$ and the like. Preferred Pd(0) cataylsts include tetrakis(triphenylphosphine) palladium (0), ([Pd(PPh$_3$)$_4$] or Pd(0) tetrakis) and bis(tri-tertbutylphosphine) palladium (0). In a preferred embodiments of Step 3, the palldium (0) catalyst [Pd] is Pd(0) tetrakis and the sustained dissolved CO concentration is maintained by a continuous subsurface addition of CO gas or by CO gas pressure. Continuous subsurface addition of CO gas or by CO gas pressure into the carbonylation reaction mixture is preferably done at a rate that provides a steady-state foam volume of ~2-8% (preferably ~4%) with respect to the total reaction mixture volume (mitigates undesired by-product formation). Preferred CO pressures range from 1 psig to 100 psig. CO pressures of 1-5 psig preferred for operating in a continuous subsurface addition of CO. CO pressures of 20 to 100 psig preferred (with 80-100 psig more preferred) for operating in a closed pressurized reactor with continuously maintained CO pressurization. Following Step 3 may be the optional step of purifying the protected ester compound (6).

A separate embodiment of the invention is a method of preparing a compound 6 from a compound 3

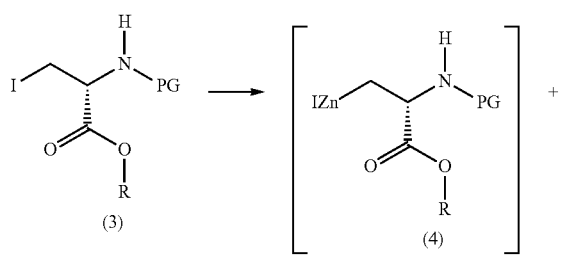

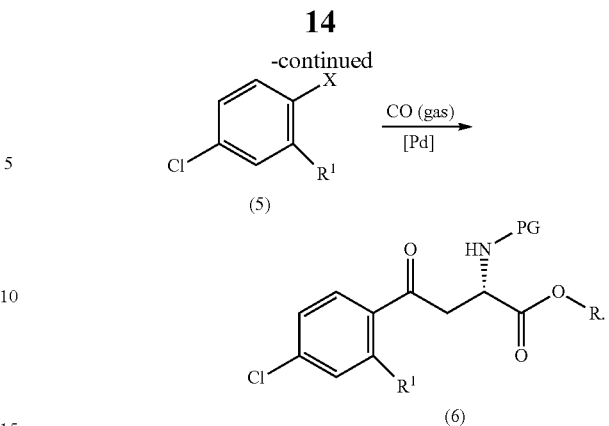

In this embodiment of the invention, the groups R, PG and R$^1$ are the same as those described above, including the preferred embodiments. The method is accomplished in the same way as just described for Step 3 of Scheme I, including its preferred embodiments. The Examples below describe additional steps and preferred embodiments of this and the other methods of the invention.

Step 4 in Scheme I deprotects the protected ester compound (6) in the absence of light under suitable reaction conditions to remove any protecting group PG, and, when R$^1$ is NO$_2$, reducing the NO$_2$ group to an NH$_2$ group, to form the ester (7), and deprotecting (hydrolyzing) the ester (7) in the absence of light without exposure to air under suitable reaction conditions to form 4-chlorokynurenine (8) after adjustment to an acidic pH. In a preferred embodiment, the reaction temperature may range from -20° to 60° C., 0° to 50° C., 10° to 40° C., 15° to 35° C.°, more preferably 20° to 30° C. The deprotecting and reducing reactions are done in a single step or in multiple steps. In a preferred embodiment, Step 4 deprotects the protected ester compound (6) to remove any protecting group PG using HCl in dioxane and isolates the ester (7) as an acid salt, such as a dihydrochloride salt, in the absence of light without exposure of the isolated solids to air or moisture. Exposure to air or moisture sensitive in the solid state may lead to unplanned/unintentional acid hydrolysis. Then, in a separate deprotection step, hydrolyzes (7) at a pH of 10.5 to 14.0, 11.0 to 13.5, 11.5 to 13.0, more preferably at a pH of 12.0 to 12.5 to form 4-chlorokynurenine (8) after adjustment to an acidic pH. The hydrolysis of (7) may be accomplished by means known in the art, such as with an aqueous base selected from LiOH, NaOH, and KOH, most preferably LiOH. That adjustment, as mentioned below, may be acidification with an aqueous acid such as HCl to a pH below 8, 7 or 6.5, preferably to a pH of 4.8 to 6.0.

Another embodiment of the invention prepares L-4-chlorokynurenine (8a) according to Scheme II above. Another embodiment of the invention are methods that prepare L-4-chlorokynurenine (8a) according to Scheme II using Steps 1-4 described below. The Examples below describe additional steps and preferred embodiments of the methods of the invention. In a method of the invention as shown in Scheme II, the overall yield to crude L-4-chlorkynurenine (8a) is 32%-39% which is a significant improvement over previous syntheses, such as the synthesis reported in WO 2014/152835 which had an overall yield of 4% to 6%.

Step 1 of Scheme II reacts a BOC-L-serine methyl methyl ester (1a) with toluenesulfonyl chloride under suitable reaction conditions to convert the BOC-L-serine methyl ester (1a) to its corresponding tosylate (2a). In a preferred embodiment, 1 to 2 molar equivalents of toluenesulfonyl chloride may be used at a reaction temperature ranging from −50° to 50° C., −40° to 40° C., −30° to 30° C., −20° to 20° C., −10° to 10° C., more preferably −5° to 5° C. In a further preferred embodiment, Step 1 is carried out in the presence of a catalytic amount of 4-dimethylaminopyridine and, optionally includes isolating and recrystallizing the tosylate (2a).

Step 2 of Scheme II reacts the tosylate (2a) with sodium iodide or potassium iodide, preferrably sodium iodide, under an inert atmosphere in the absence of light under suitable reaction conditions to replace the tosyl group with iodide and form the corresponding iodo intermediate (3a). In a preferred embodiment, the reaction temperature may range from −20° to 60° C., −10° to 50° C., 0° to 40° C., more preferably 10° to 30° C. In a preferred embodiment, Step 2 includes an aqueous quench of the reaction mixture into water at a temperature ranging from 0° to 40° C., 0° to 30° C., 0° to 20° C., and more preferably 0° to 10° C., to precipitate the iodo intermediate (3a) and, optionally, recrystallization of the iodo intermediate (3a).

Step 3 of Scheme II converts the iodo intermediate (3a) in situ to a zinc reagent (4a) in the absence of light under suitable reaction conditions and forming a BOC-protected methyl ester compound (6a) via a carbonylation reaction and reacting the zinc reagent (4a) with a 5-chloro-iodo aniline compound (5a) in the presence of a palladium (0) catalyst [Pd] and while maintaining a sustained dissolved CO concentration either by continuous subsurface CO addition and/or CO pressure. In a preferred embodiment the conversion of intermediate (3a) in situ to a zinc reagent (4a) may be done at a reaction temperature ranging from 0° to 50° C., 10° to 40° C., 15° to 35° C., more preferably 23° to 27° C. or 25° C., and then carbonylation reaction at a reaction temperature ranging from 15° to 35° C., more preferably 20° to 26° C. Palladium (0) catalysts used for coupling reactions may be used. See, e.g., Colacot, Platinum Metials Rev., 2012, 56, (2), 110-116. Ligands for Pd(0) catalysts include for example dppm, dppe, dppp, dcpe, PPh$_3$, P(cyclohexyl)$_3$, P(t-Bu)$_3$, P(C$_6$F$_5$)$_3$, P(2,4,6-MeC$_6$H$_2$)$_3$ and the like. Preferred Pd(0) cataylsts include tetrakis(triphenylphosphine) palladium (0), ([Pd(PPh$_3$)$_4$] or Pd(0) tetrakis) and bis(tri-tertbutylphosphine) palladium (0). In a preferred embodiments of Step 3, the palldium (0) catalyst [Pd] is Pd(0) tetrakis and the sustained dissolved CO concentration is maintained by a continuous subsurface addition of CO gas or by CO gas pressure. Continuous subsurface addition of CO gas or by CO gas pressure into the carbonylation reaction mixture is preferably done at a rate that provides a steady-state foam volume of ~2-8% (preferably ~4%) with respect to the total reaction mixture volume (mitigates undesired by-product formation). Preferred CO pressures range from 1 psig to 100 psig. CO pressures of 1-5 psig preferred for operating in a continuous subsurface addition of CO. CO pressures of 20 to 100 psig preferred (with 80-100 psig more preferred) for operating in a closed pressurized reactor with continuously maintained CO pressurization. Following Step 3 may be the optional step of purifying the protected ester compound (6a).

A separate embodiment of the invention is a method of preparing a compound 6a from a compound 3a

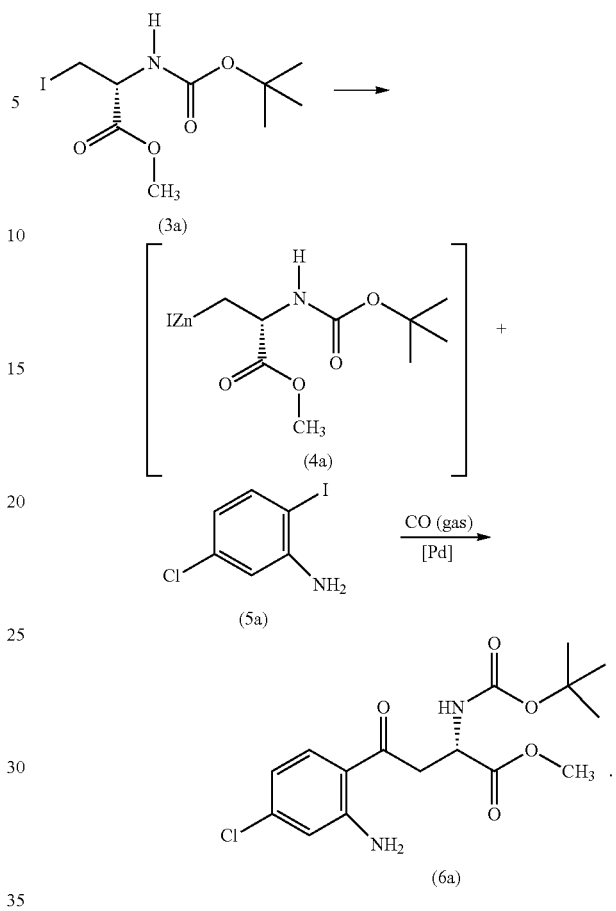

In this embodiment of the invention, preparation of (6a) is accomplished in the same way as just described for Step 3 of Scheme II, including its preferred embodiments. The Examples below describe additional steps and preferred embodiments of this and the other methods of the invention.

Step 4 in Scheme II deprotects the BOC protected ester compound (6a) in the absence of light under suitable reaction conditions to remove the protecting group to form the methyl ester (7a) taking precautions to avoid exposing the isolated solids to air or moisture, and then deprotecting (hydrolyzing) the methyl ester (7a) in the absence of light without exposure to air under suitable reaction conditions to form 4-chlorokynurenine (8a) after adjustment to an acidic pH. In a preferred embodiment, the reaction temperature may range from −20° to 60° C., 0° to 50° C., 10° to 40° C., 15° to 35° C.°, more preferably 20° to 30° C. The deprotecting and reducing reactions are done in a single step or in multiple steps. In a preferred embodiment, Step 4 deprotects the BOC protected methyl ester compound (6a) using HCl in dioxane and isolates the methyl ester (7a), such as a dihydrochloride salt, in the absence of light without exposure of the isolated solids to air or moisture. Air or moisture exposure may lead to unplanned/unintentional acid hydrolysis. Then, in a separate deprotection step, hydrolyzes (7a) at a pH of 10.5 to 14.0, 11.0 to 13.5, 11.5 to 13.0, more preferably at a pH of 12.0 to 12.5, to form 4-chlorokynurenine (8a) after adjustment to an acidic pH. The hydrolysis of (7) may be accomplished by means known in the art, such as with an aqueous base selected from LiOH, NaOH, and KOH, most preferably LiOH. That adjustment, as mentioned below, may be acidification with an aqueous acid such as HCl to a pH below 8, 7 or 6.5, preferably to a pH of 4.8 to 6.0.

A separate embodiment of the invention is a method for the preparation of L-4-chlorokynurenine (8a) from a compound (6a)

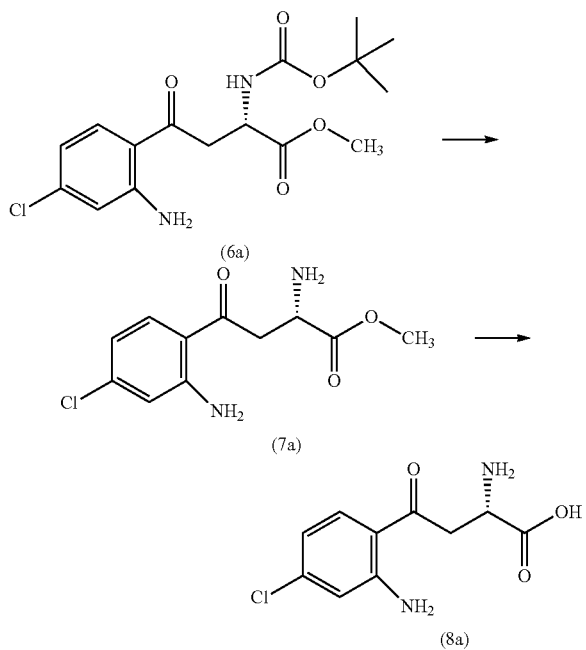

In this embodiment of the invention, preparation of (8a) is accomplished in the same way as just described for Step 4 of Scheme II, including its preferred embodiments. The Examples below describe additional steps and preferred embodiments of this and the other methods of the invention.

In another embodiment the invention also relates to a compound of the formula (6a):

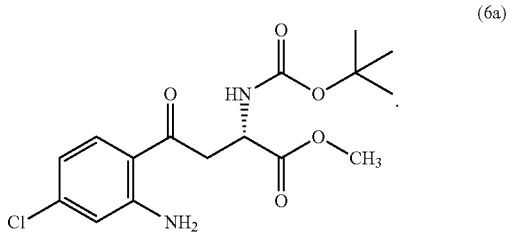 [SMILES: COC(=O)[C@H](CC(=O)c1ccc(Cl)cc1N)NC(=O)OC(C)(C)C]

In another embodiment the invention also relates to a compound of the formula (7a):

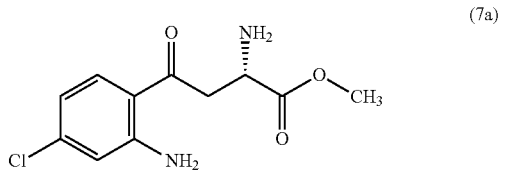 [SMILES: COC(=O)[C@@H](N)CC(=O)c1ccc(Cl)cc1N]

or a acid addition salt thereof. Preferably the acid addition salt is a di-HCl salt.

Methods of the invention according to Scheme I or Scheme II, may include further steps to purify the 4-chlorokynurenine product (8) in Scheme I or the L-4-chlorokynurenine product (8a) in Scheme II. Those purification steps may include the steps of, as the pH adjustment, isolating the 4-chlorokynurenine (8)/L-4chlorokynurenine (8a) from alkaline solution as a fee acid with aqueous acid, e.g. HCl, to a pH below 8, 7 or 6.5, preferably a pH of 4.8 to 6.0; dissolving the isolated free acid (8)/(8a) in aqueous acid at a pH below 2, preferably a pH of 0.5 to 0.9; precipitating the free acid (8)/(8a) by adjusting the pH of 4.5 to 6.5, preferably a pH of 4.8 to 6.0; collecting the precipitated free acid (8)/(8a); drying the collected free acid (8)/(8a), and optionally, triturating the collected free acid (8)/(8a) using an organic solvent or an organic solvent mixture as known n the art and drying the triturated free acid (8)/(8a). Precipitating the free acid (8)/(8a) may be done by adding a base, such as aqueous ammonia, as is known the art. The organic solvents in the optional trituraitng step may be methanol/ethyl acetate.

The methods of the invention have improved process conditions suitable for safe, efficient, and scaleable stereocontrolled manufacture of 4-chlorokynurenine compounds (8) and in particular L-4-chlorokynurenine (8a) which overcoming the limitations of previously reported syntheses. In the methods of the invention, process conditions have been developed to mitigate and control impurity formation, particularly in Step 4 and Step 5. For example, such improved conditions include (but are not limited to):

Fresh preparation of iodo-substituted protected amino acid to mitigate decomposition.

Pre-saturation of the Pd catalyst with carbon monoxide to mitigate unwanted side reactions.

Maintaining efficient introduction and presence of carbon monoxide to ensure high carbon monoxide activity and availability to Pd catalyst to mitigate unwanted side reactions either through continuous subsurface CO flow or CO pressure.

Controlled inverse addition of protected amino acid zincate to the iodoaniline and Pd catalyst pre-coordinated with carbon monoxide (as distinct from the prior art conditions comprising "all in" addition of aromatic iodide and Pd catalyst to the zincate). See Jackson et al., JCS Perkin 1, 1997, 865. See also Dunn et al., SYNLETT, 1993, 499 describing a serine-derived organozinc reagent in THF and its use in the synthesis of novel, enantiomerically pure allenic, acetylenic and heteroaryl amino acids.

Controlled addition of reagents to mitigate rate of reaction and rate of heat evolution to better control reaction temperature on scale up for improved safety on scale up and for improved reaction selectivity and improved product quality on scale up.

Avoiding the need for low loading fractional chromatography by means of improved reaction selectivity.

Adoption of two step deprotection after coupling for improved reaction control, selectivity, efficiency and decreased by products by use of HCl in wet dioxane for amino BOC deprotection to give the final product ester dihydrochloride salt followed by separate ester hydrolysis under controlled mildly basic conditions followed by controlled acidification to isolate 4-chlorokynurenine products (8), such as L-4-chlorokynurenic acid (8a) as zwitterionic neutral form. This avoids increased reaction sensitivity to by-product formation when using the single acidic double deprotection from (6) to (8)/(6a) to (8a) that is described in the prior art (Jackson et al.) which also gives increased propensity to formation of an unwanted byproduct and other decomposition by-product pathways.

Recognition of product and intermediates sensitivity to light, heat, acid and base to mitigate decomposition by mitigating exposure to such conditions.

EXAMPLES

Examples 1-5 below demonstrate lab-scale and large-scale synthesis of L-4-chlorokynurenine according to the processes of the invention and as shown in Schemes I and II (above). Examples 1-5 also describe the process improvements of the invention, which individually and in combination are embodiments of the processes of the invention. The product L-4-chlorokynurenine may be further purified by means known in the art and as described below.

Example 1—Step 1

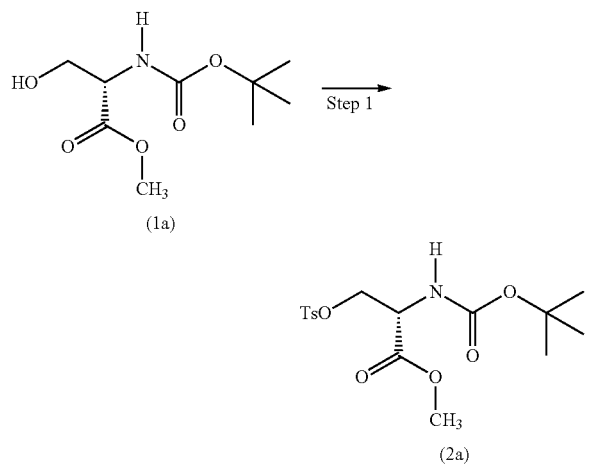

Example 1.1—Step 1: Lab Scale

A 2 liter round bottom flask was charged with a mechanical overhead stirrer, BOC-L-serine methyl ester (1a) (0.91 mol), and pyridine (800 mL) under an atmosphere of nitrogen. After cooling to 0-5° C., 4-dimethylaminopyridine (91 mmol) was charged to the flask. Toluenesulfonyl chloride (1.36 mol) was charged in 4 portions over a total of 30 minutes. After stirring at 0-5° C. for 26 h, 0.25 mL of the reaction mixture was extracted using water (20 mL) and dichloromethane (20 mL). The organic layer was evaporated to leave a pale yellow oil. Then 20 mg of the oil were dissolved in $CDCl_3$ for determination of the conversion of BOC-L-serine methyl ester (1a) to the corresponding tosylate (2a) by $^1H$ NMR spectroscopy. After completion of the reaction, the reaction mixture was added to 0-5° C. water (3 L) of over 1 h. Then the mixture was stirred for 2 h at 0-5° C., during which time a white solid precipitated out. Solids were then filtered through a fritted funnel, rinsed with water (3×400 mL), and allowed to deliquor for 16 hours. The crude solids were charged to a 5 L round bottom flask along with tert-butyl methyl ether (1 L). The solution was warmed to 40° C., at which point all solids had dissolved. A phase separation was performed and the lower aqueous layer was drained and discarded. While maintaining the temperature at 35-40° C., water (30 mL) was charged to the flask and stirred for 5 minutes. Stirring was stopped and the lower aqueous layer was drained and discarded. At 35-40° C., heptane (2 L) was added over 45 minutes to the remaining organic layer. After the complete addition of heptane, the solution was cooled to 0-5° C. and stirred for 2 h. The white solids were filtered using a fritted funnel. The flask was rinsed using the filtrate then washed with clean heptane (2×20 mL). The solids were deliquored for 1 h then placed in a vacuum drying oven at ambient temperature for 20 hours, resulting in pure product 2a in 82% yield.

Example 1.2—Step 1: Large Scale

Synthesis of 2a:

1a (7.00 Kg, 31.93 moles, 1.00 equiv) was weighed into a clean and dry container and then charged into a nitrogen-purged 50-L glass reactor (Reactor A). Anhydrous pyridine (27.38 Kg, 4 vol) was charged into the reactor. Some pyridine was used to rinse the container used for 1a and the rinse was then charged into the reactor. The reaction mixture was stirred under nitrogen for ~9 minutes at ~15° C. (target: 10-30° C.) and then cooled to −3.4° C. (target: ~5° C. to 0° C.) over one hour and 46 minutes. Pre-weighed DMAP (392.0 g, 3.209 moles, 0.10 equiv) in a clean and dry container was charged into the reactor in one portion. The reaction mixture was stirred for 5 minutes at −3.7° C. TsCl (9.1 Kg, 1.5 equiv) was charged in four portions over one hour and 36 minutes at −5° C. to 0° C. The first TsCl portion (2.28 Kg) was charged into the reactor over 5 minutes. The reaction mixture was stirred for 41 minutes. The second TsCl portion (2.26 Kg) was charged into the reactor over 4 minutes. The reaction mixture was stirred for 20 minutes. The third TsCl portion (2.29 Kg) was charged into the reactor over 2 minutes. The Reaction mixture was stirred for 19 minutes. The fourth and final TsCl portion (2.27 Kg) was charged into the reactor over 5 minutes.

The reaction mixture was then stirred for 18 hours and 41 minutes at 0±5° C. and then checked by $^1H$ NMR. The reaction was incomplete with 1.5% of 1a (integration relative to 2a). The reaction was stirred for an additional one hour and 44 minutes at 0±5° C. and then checked by $^1H$ NMR. The results showed that the reaction was complete with 1.4% of 1a remaining (integration relative to 2a).

Preciptation of Crude 2a:

Based on the total work-up volume required (~150 L), the precipitation of the product in two portions was done using two reactors (50-L and 100-L). The total reaction volume prior to the work up was ~42 L. One third of the reaction volume was to be transferred into a 50-L reactor (Reactor B) for precipitation and two thirds of the reaction volume was to be transferred into a 100-L reactor (Reactor C) for precipitation.

Precipitation #1:

Deionized (DI) water (34.99 Kg, 15 vol to 1a) was weighed out into clean containers and pre-cooled in a refrigerator, then charged into Reactor B. The batch was cooled to 4.5° C. (target: 3-10° C.). A portion of the reaction mixture (~14 L, ⅓ of batch) was slowly transferred into the cold water over one hour and 25 minutes. Initially, two liters of the reaction mixture were transferred, the addition was paused, and the quench mixture was stirred for 45 minutes. Solid precipitation was observed immediately, but some oily products precipitated on the cold reactor wall (Jacket temperature set point: 1° C.). In order to avoid the oil precipitation on the cold wall, the jacket temperature was increased to 5° C. which increased the batch temperature to 12.1° C.

Transfer of the reaction mixture resumed and after complete transfer of reaction mixture, the pre-weighed pyridine (1.14 Kg, for transfer rinsing) was charged. The quenched batch was stirred for 61 minutes at 10±2° C. The slurry was transferred into the filter funnel. Since the bottom valve was blocked with some sticky solids, the batch was transferred from the top using a vacuum suction tube. The filtration of the slurry took about two hours and the wet cake was deliquored for 10 minutes. The wet cake in the filter funnel was washed with water (4×4.67 kg, or 4×2 vol to 1a) and deliquored for 14 hours by applying vacuum to the filter funnel to afford 8.09 kg of wet, crude 2a.

Precipitation #2:

DI water (70 Kg, 15 vol to 1a) was weighed out into clean containers and pre-cooled in a refrigerator, then charged into Reactor C. The quench water was cooled to 6.5° C. (target: 3-10° C.). Of the planned ~28 L total reaction mixture transfer, ~14 L of the reaction mixture were transferred into the cold water over 5 minutes due to operator error. A large oil layer precipitated in the bottom of the quench mixture and suddenly solidified. Some of the precipitated solids accumulated in the bottom of the reactor and caused the agitator to seize. The batch transfer into the quench was stopped. The quenched material in Reactor C was settled for 5 hours at 0-10° C.

The upper clear solution (~40 L) in Reactor C was transferred into Reactor B (used for previous precipitation). The remaining unquenched reaction mixture (~14 L) from Reactor A was slowly transferred into Reactor B for pre-cipitation of 2a over 40 minutes at 0-15° C. The resulting slurry was stirred for 17 hours at 0-15° C.

The quenched batch portion from Reactor C was settled for 20 hours at 5° C. and then transferred into the filter funnel. Since the bottom valve was blocked with some solids, the batch was transferred out from the top under vacuum. During the transfer, re-cycled filtrate was used to rinse Reactor C forward to the product cake on the filter funnel. After completion of the batch transfer from Reactor C, the batch portion from Reactor B was transferred onto the top of the filter cake in the filter funnel. The filtration required 6 hours. The wet cake was then washed with water (4×9.33 Kg, or 4×2 vol to 1a) and finally deliquored for 15 hours and 30 minutes by applying vacuum to afford 20.34 Kg of wet, crude 2a.

The water quench/precipitation works well at lab scale, Example 1.1, but provides an unstirrable mixture if the mixing conditions are not carefully controlled at large scale. Crude 2a should be precipitated by adding the reaction mixture in pyridine into cold water with a carefully controlled addition to ensure even precipitation. Addition of the reaction mixture into the cold water quench must be slow and well controlled especially at the beginning of addition. Utilization of flow controlled pumps to simultaneously co-mix the quench water with the reaction mixture (~3:1 v/v) provides well controlled precipitation. Even with slow addition, some oily precipitation on the walls of the reactor was observed. Stirring overnight was sufficient to convert all of the oily material into filterable solids. After quench and precipitation of crude 2a, stirring the slurry at 0-15° C. for at least 12 hours yields an easily transferable slurry. Utilization of flow controlled pumps to simultaneously co-mix the quench water with the reaction mixture (~3:1 v/v) provides well controlled precipitation.

Purification of Wet, Crude 2a:

The combined wet, crude 2a (28.43 Kg) was transferred into Reactor A under nitrogen in portions using MTBE (25.90 Kg, 5 vol to 1a) to slurry the solids to facilitate the transfer. The batch was heated to 45° C. and stirred for 18 minutes at 45-47° C. to obtain a clear solution (biphasic). The bottom aqueous layer (~20 L) was removed. The batch was washed with water (1.4 L, 0.2 vol) and the lower water layer was removed. The batch was refluxed for one hour and 45 minutes under vacuum (419-630 Torr) at 40-50° C. to remove about 75 mL of water (Dean-Stark trap collection). The batch was transferred into Reactor C. Heptane (47.88 Kg, 10 vol to 1a) was added into Reactor C over 62 minutes while maintaining the batch temperature at 30-50° C. The slurry was cooled to 0±5° C. over three hours and stirred for 12 hours 40 minutes at 0±5° C. The batch was transferred into a filter funnel over one hour and 45 minutes. Since the bottom valve was blocked with some solids, the batch was transferred out from the top using vacuum suction. During the transfer, the re-cycled filtrate was used to rinse the reactor forward to the filter funnel. The filter cake was washed with cold heptane (9.58 Kg, 0° C., 2 vol to 1a) and then deliquored for one hour and 40 minutes. The wet filter cake (13.389 Kg) was transferred into 10 glass drying trays and dried under vacuum 50 Torr) at 20-40° C. over 72 hours to afford dried 2a (9.388 Kg, 79% yield).

Example 1.3—Step 1: Large Scale Preparation of 2a

Synthesis of 2a (Reaction):

1a (7.00 Kg, 31.93 moles, 1.00 eq.) was weighed into a clean and dry container and then charged into a nitrogen-purged 50-L glass reactor. Anhydrous pyridine (27.40 Kg) was charged into the reactor. The reaction mixture was stirred under nitrogen for ~20 minutes at ~22° C. (target: 10-30° C.) and then cooled to −1.8° C. (target: −5° C. to 0° C.) over two hours and one minute. Pre-weighed DMAP (392 g, 3.21 moles, 0.10 eq.) in a clean and dry container was charged into the reactor in one portion. The reaction mixture was stirred for 15 minutes at −2.7 to −3.9° C. Tosyl Chloride (TsCl) (9.10 Kg, 1.5 eq.) was charged in four portions over two hours and 56 minutes at −5° C. to 0° C.

The first TsCl portion (2.30 Kg) was charged to the reactor over 4 minutes. The reaction temperature was adjusted to −5 to 0 C over one hour and 41 minutes. The reaction mixture was stirred for 20 minutes at −5° C. to 0° C.

The second TsCl portion (2.22 Kg) was charged to the reactor over one minute. The reaction temperature was adjusted to −5 to 0° C. over 13 minutes. The reaction mixture was stirred for 10 minutes at −5° C. to 0° C.

The third TsCl portion (2.30 Kg) was charged over 3 minutes. The reaction temperature was adjusted to −5 to 0° C. over 5 minutes. The reaction mixture was stirred for 12 minutes at −5° C. to 0° C.

The fourth and final TsCl portion (2.28 Kg) was charged to the reactor over 4 minutes. The reaction temperature was adjusted to −5 to 0° C. over one minute. The reaction mixture was stirred for 15 minutes at −5° C. to 0° C.

The reaction mixture was adjusted to −5° C. to 5° C. over 13 minutes, then stirred for 16 hours and 20 minutes at 0±5° C. and then sampled and checked by $^1$H NMR. The reaction was incomplete with 0.02% of 1a with respect to 2a remaining (target: 0.01). The reaction was stirred for an additional one hour and 35 minutes at 0±5° C. and then sampled checked by $^1$H NMR. The results showed that the reaction was complete with 0.01% of 1a with respect to 2a remaining.

Precipitation of Crude 2a (Product Isolation):

Based on the total calculated work-up volume (~150 L) for this batch, the batch record called for the precipitation of the product in two reactors (50-L and 100-L). The total reaction volume was ~45 L. Two thirds of the reaction volume was to be transferred into a 100-L reactor for the precipitation and one third of the reaction volume was to be transferred into a 50-L reactor for the precipitation.

Precipitation #1 in 100-L Reactor (for ⅔ of batch) and Isolation of Crude 2a:

DI water (70.01 Kg) was weighed into clean carboys and pre-cooled in a refrigerator (6-7° C.). Pre-chilled DI water (~3.5 L) was transferred into a 100 L reactor via a peristaltic pump and then pyridine (1.27 Kg) was added. Note: The ratio of DI water and pyridine in the reactor at this step should be approximately 10:3 (v/v). The mixture was adjusted to 6.8° C. (target: 3-10° C.). The entire pre-chilled DI water in carboys and 30 L of the reaction mixture were simultaneously transferred into the 100 L reactor via two peristaltic pumps over 167 minutes while maintaining the batch temperature at 3-10° C. The transfer line for the reaction mixture was rinsed forward with pyridine (1.26 Kg). The batch was adjusted to 6.6° C. (target: 0-10° C.). The reaction mixture was stirred for 17 hours at 0-10° C. and filtered in a filter funnel over 9 hours. The filter cake was de-liquored in the filter funnel for 30 minutes by applying vacuum to the filter funnel. The wet cake was then washed with DI water (4×9.33 Kg) and suction dried in the filter funnel for 9 hours 29 minutes by applying vacuum to the filter funnel to afford the crude 2a wet cake (Load #1, 21.65 Kg).

Precipitation #2 in 50-L Reactor (for ⅓ of batch) and Isolation of Crude 2a:

DI water (35.01 Kg) was weighed out into clean carboys and pre-cooled in a refrigerator (7° C.). Pre-chilled DI water (~1.75 L) was transferred into a 50 L reactor via a peristaltic pump and pyridine (0.51 Kg) was added. Note: The ratio of DI water and pyridine in the reactor at this step should be approximately 10:3 (v/v). The mixture was adjusted to 3.2° C. (target: 3-10° C.). The entire pre-chilled DI water in carboys and 15 L of the reaction mixture remaining (total remaining) were simultaneously transferred into the 50 L reactor via two peristaltic pumps over 113 minutes while maintaining the batch temperature at 3-10° C. The transfer line for the reaction mixture was rinsed forward with pyridine (0.63 Kg). The batch was adjusted to 8.6° C. (target: 0-10° C.). The reaction mixture was stirred for 15 hours and 47 minutes at 0-10° C. and filtered in a filter funnel over 5 hours and 33 minutes. The filter cake was de-liquored in the filter funnel for 25 minutes by applying vacuum to the filter funnel. The wet cake was then washed with DI water (4×4.67 Kg, or 4×2 L/Kg 1a input) and suction dried in the filter funnel for 14 hours by applying vacuum to the funnel to afford the crude 2a wet cake (Load #2, 10.20 Kg).

Purification of the Crude 2a (Re-Crystallization):

The combined wet, crude 2a (31.85 Kg) was transferred into a 50 L reactor and MTBE (25.91 Kg) was added under nitrogen. The mixture was heated to 42-44° C. and stirred for 15 minutes at 44-45° C. to obtain a clear solution (biphasic, no rag layer observed). The bottom aqueous layer (~24 L) was removed. The batch was washed with water (2.8 L) and the lower water phase was removed. The batch was refluxed under vacuum (400-500 Torr) at 37-45° C. for one hour and 50 minutes using a Dean-Stark Trap to remove about 155 mL of water. The batch was transferred into a 100 L reactor. The solution was diluted by adding n-heptane (47.90 Kg) into the 100 L reactor over 80 minutes while maintaining the batch temperature at 45-48° C. The slurry was cooled to 1.13° C. (target: 0±5° C.) over 14 hours and 40 minutes and stirred for 2 hours at 1.1° C. (target: 0±5° C.). The batch was transferred into a filter funnel over 15 minutes. The filter cake in the filter funnel was de-liquored by applying vacuum to the filter funnel for 15 minutes and then washed with cold n-heptane (9.60 Kg, 0° C.) and then de-liquored for 3 hours. The wet filter cake was transferred into drying trays and dried under vacuum 50 Torr) at 20-40° C. over 24 hours to afford dried 2a (9.75 Kg, 81.8% yield). NMR purity ($^1$H NMR) was 99% with 0.59% residual water content by KF titration.

Preferred Process Parameters and Embodiments within Step 1—Preparation of 2/2a

Listed below are certain preferred process parameters for Step 1 in the synthese of the invention as shown in Schemes I, II and III above. Each preferred process parameter described for a particular step, such as this step, is a separate embodiment of the invention. The preferred process parameters in each step may be employed together with those of other steps such that each combination of preferred process parameters is also a separate embodiment of the invention. A synthesis according to the invention having one or more preferred process parameters in one or more steps is also a separate embodiment of the invention. Preferred process parameters for Step 1 include, but are not limited to:

Reaction temperature −5° to 0° C. during Tosyl chloride addition (warmer leads to unwanted alkene by-product);

Reaction temperature −5° to 5° C. for reaction completion (warmer leads to unwanted alkene by-product);

Final molar ratio of staring material to product 0.01 at the reaction end point (higher leads to unwanted downstream impurities);

Recrystallization temperature maximum 45° C. (warmer leads to unwanted alkene by-product), Drying temperature 20° to 40° C. (warmer leads to unwanted alkene by-product);

2/2a Purity ≥98% (NMR);

A range of 1.0-2.0 (preferably 1.5) molar equivalents of Tosyl Chloride with respect to 1/1a (less leads to unwanted downstream impurities and more can also lead to unwanted downstream impurities);

A range of 0.01 to 0.20 (preferably 0.10) molar equivalents (catalytic amount) of 4-dimethylaminopyridine as a catalyst to enhance the reaction rate (lesser amounts can reduce or eliminate effectiveness and more can lead to unwanted downstream impurities);

Controlled addition of Tosyl chloride (rate and/or portion control) as needed to maintain the reaction temperature at −5° to 0° C. during the Tosyl chloride addition (mitigates formation of unwanted alkene by-product);

Isolation of 2/2a by a temperature controlled (0-10° C.) precipitation and granulation of the reaction mixture from a water/pyridine mixture with a final ratio of water/pyridine of ~10/3 (v/v) (mitigates formation of unwanted alkene by-product); and/or Recrystallization of 2/2a from a mixture of Methyl-tert-butyl ether (MTBE)/n-Heptane (0.5-0.6/1.0, w/w, preferably 0.54/1.0 w/w) (provides control of final purity).

Example 2—Step 2

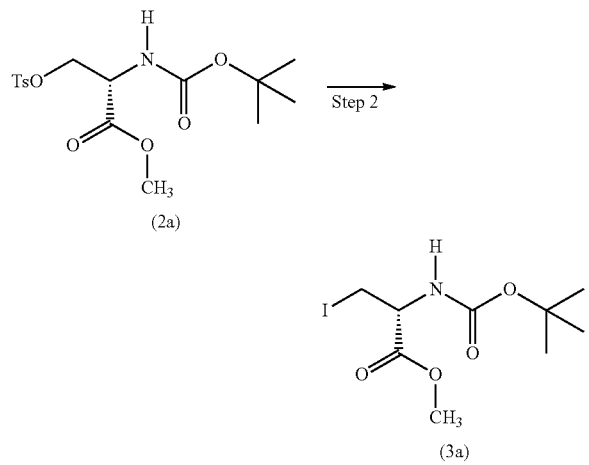

Example 2.1—Step 2: Lab Scale

The entire following procedure was performed in the dark. A 2-liter round bottom flask covered in foil was charged with the tosylate of BOC-L-serine methyl ester 2a (0.40 mol) and acetone (855 mL) under an atmosphere of nitrogen. While stirring, sodium iodide (1.0 mol) was added in one portion and allowed to stir for 22 h, at which time the reaction was complete by thin layer chromatography (30% ethyl acetate in heptane, $KMnO_4$ stain, disappearance of 2a). The reaction mixture was added slowly over 1 h to 0-5° C. water (3 L) and stirred for 2 h at that temperature. The crude solids were filtered using a fritted funnel, washed with water (3×50 mL), then deliquored for 16 h. A 1-liter round bottom flask was charged with the crude solids and heptane (225 mL). The mixture was warmed to 35-40° C. at which point all of the solids had dissolved. A phase separation was performed and the lower aqueous layer was drained and discarded. The organic layer was cooled to −15° C. and stirred for 2 h. The solids were filtered using a fritted funnel and rinsed twice with the filtrate, then with clean, 0° C., heptane (20 mL). The solids were dried in a vacuum drying oven at ambient temperature for 24 h, providing pure iodo-intermediate 3a in 80% yield.

Example 2.2—Step 2: Large Scale

Synthesis of 3a:

2a (9.32 Kg, 24.96 moles, 1.00 equiv) was weighed and charged into a nitrogen-purged 100-L glass reactor (Reactor A). Acetone (42.0 Kg, 5.7 vol) was charged into Reactor A. The reaction mixture was stirred under nitrogen for 6 minutes at ~15° C. (target: 10-30° C.) to dissolve the solids. The reactor was covered with aluminum foil since the reaction mixture is light sensitive. NaI (9.36 Kg, 2.50 equiv) was charged into Reactor A over 30 minutes while maintaining the batch temperature at 10-30° C. The reaction was slightly exothermic: Portion #1: the temperature increased from 23.4° C. to 25.7° C. when 2 Kg NaI was added in one portion (jacket temperature at 20° C.); Portion #2: the temperature increased from 25.7° C. to 27.6° C. when 2 Kg NaI was added in one portion (jacket temperature at 20° C.). External cooling (jacket temperature at 20° C.) and addition control of the remaining portions were used to maintain the process temperature within the target range. The reaction mixture was stirred for 21 hours and 30 minutes at 20-30° C. and then checked by TLC. The reaction was complete by TLC because the 2a spot had completely disappeared.

Precipitation of Crude 3a:

Based on the total work-up volume required (~260 L in total), the precipitation of the product was done in three portions in a 100-L reactor (~87 L each, Reactor A). The total reaction mixture volume prior to work up was ~66 L. The reaction mixture was transfer from Reactor A into two 50-L reactors (Reactor B and Reactor C) covered with aluminum foil. One third of the reaction volume (~22 L) was transferred into a 50-L reactor (Reactor B) for one precipitation and two thirds of the reaction volume (~44 L) was transferred into another 50-L reactor (Reactor C) for use in two precipitations.

Precipitation #1 and Filtration #1A:

DI water (62.10 Kg, 20 vol to 2A) was weighed out into clean containers and pre-cooled in a refrigerator, then charged into Reactor A. The quench water was cooled to 4.8° C. (target: 0-5° C.). The reaction mixture (~22 L) in Reactor B was slowly transferred into the cold water in Reactor A over one hour and 13 minutes while maintaining the batch temperature at 0-10° C.; overall addition rate: ~2 L/5 minutes. Initially, two liters of the reaction mixture were transferred, the addition was paused, and the quench mixture was stirred for 5 minutes. Solid precipitation was observed immediately. The addition was resumed and after the addition was complete, the batch was stirred for 84 minutes at 5±5° C. The batch was smoothly transferred into the filter funnel over 33 minutes. The batch was deliquored on the filter funnel for one hour.

Precipitation #2 and Filtration #1B:

DI water (62.11 Kg, 20 vol to 2a) was weighed out into clean containers and pre-cooled in a refrigerator, then charged into Reactor A. The quench water was cooled to 4.5° C. (target: 0-5° C.). The reaction mixture (~22 L, ½ of batch from Reactor C) was slowly transferred into the cold water in Reactor A over 42 minutes while maintaining the batch temperature at 0-10° C.; overall addition rate: ~2 L/4 minutes. Initially, two liters of the reaction mixture were transferred, the addition was paused, and the quench mixture was stirred for 5 minutes. Solid precipitation was observed immediately. The addition was resumed and after the addition was complete, the batch was stirred for 48 minutes at 5±5° C. The batch was smoothly transferred onto the filter cake in the funnel from previous filtration over 17 minutes. The batch was deliquored for 13 minutes. The wet cake in the filter funnel was washed with water (4×31.1 Kg, or 4×5 vol to 2a) and finally deliquored for 2 hours by applying vacuum to the filter funnel to afford 8.92 Kg of wet, crude 3a.

Precipitation #3 and Filtration #2:

DI water (62.17 Kg, 20 vol to (2a)) was weighed out into clean containers and pre-cooled in a refrigerator, then charged into Reactor A. The quench water was cooled to 2.6° C. (target: 0-5° C.). The reaction mixture (~22 L, ½ of batch from Reactor C) was slowly transferred into the cold water in Reactor A over one hour while maintaining the batch temperature at 0-10° C.; overall addition rate: ~2 L/5 minutes. Initially, two liters of the reaction mixture were transferred, the addition was paused, and the quench mixture was stirred for 5 minutes. Solid precipitation was observed immediately. The addition was resumed and, after the addition was complete, the batch was stirred for 71 minutes at 5±5° C.

The batch was smoothly transferred into the filter funnel over 25 minutes. The batch was deliquored for 12 minutes. The wet cake in the filter funnel was washed with water (4×15.5 Kg, or 4×5 vol to 2a) and finally deliquored for 2 hours by applying vacuum to the filter funnel to afford 3.49 Kg of wet, crude 3a.

Crude 3a should be precipitated by adding the acetone reaction mixture into cold water in a well controlled manner. Initially, ~2 liters (out of 22 L total) of the reaction mixture was added into the cold water quench and the quench mixture was stirred for 5 minutes to form uniform slurry and then the remaining (~20 L) reaction mixture then continuously added over ≥1 hour. The resulting slurry was uniform and easily filtered.

Purification of Wet, Crude 3a:

The combined wet, crude 3a (12.41 Kg) was transferred into Reactor B under nitrogen followed by heptane (9.58 Kg, 1.5 vol to (2A)). The batch was heated to 39.5° C. and stirred for 5 minutes at ~39° C. to obtain a clear solution (biphasic). The bottom aqueous layer (~5 L) was removed. The batch (~20 L) was cooled to 20° C. over one hour and 13 minutes. During the cooling, 3a crystallization occurred at ~29° C. The slurry was stirred for one hour at 10-20° C. and then cooled to −22.8° C. over 16 hours and 45 minutes. The cold batch was stirred for 2 hours and 20 minutes at −20±5° C. The batch was transferred into a filter funnel contained in a large PE bag under a nitrogen purge over 35 minutes. During the transfer, re-cycled filtrate was used to rinse the reactor forward to the product cake on the filter funnel. After deliquoring for 11 minutes under nitrogen, the filter cake was then washed with cold heptane (3.19 Kg, 0° C., 0.5 vol to (2a)) and then deliquored for two hours and 6 minutes under nitrogen. The wet filter cake (7.74 Kg) was transferred into 6 glass drying trays and dried in a vacuum oven 50 Torr) at ambient temperature for one hour and 26 minutes and then at 20-30° C. 50 Torr) over 70 hours to afford dried (3a) (6.85 Kg, 83.3% yield (6.85 Kg, 83% Yield, 99.29% AUC purity). The final water content after drying was only 0.013.

Transfer of the slurry of purified 3a in heptane at −20±5° C. into the filter funnel was slow. Since the heptane volume was very low (only 1.5 vol for the re-crystallization), the solids settled and recycled mother liquor was required to rinse the residual solids from the reactor. The residual solids from the reactor were easy to rinse forward into the filter funnel. Since (3a) is light sensitive, the whole process should minimize light exposure as much as feasible. 3a is also very sensitive to air and the filtration must be done under a nitrogen atmosphere. (in lab experiments with de-liquoring of the wet cake by applying vacuum to the filter funnel without nitrogen protection caused the (3a) to turn dark (brown) on the top of the filter cake). The Kilo Lab filtration operations were carried out in a large PE bag under a constant nitrogen purge to minimize air exposure.

Example 2.3—Step-2: Large Scale Preparation of 3a

Synthesis of 3a (Reaction):

2a (9.69 Kg, 25.96 moles, 1.00 eq.) was weighed and charged into a nitrogen-purged 100-L glass reactor (Reactor A). Acetone (43.70 Kg) was charged into Reactor A. The reaction mixture was stirred under nitrogen for 10 minutes at ~15° C. (target: 10-30° C.) to dissolve the solids. The reactor was covered with aluminum foil to exclude light since the reaction mixture is light sensitive. NaI (9.73 Kg, 2.50 eq.) was charged into Reactor A over 22 minutes while maintaining the batch temperature at 10-30° C. The reaction mixture was stirred for 16 hours and 15 minutes at ~25° C. (target: 20-30° C.) and then checked by TLC. The reaction was complete with 2a non-detected by TLC.

Precipitation of Crude 3a (Crude Product Isolation):

Based on the total work-up volume required (~268 L in total), the batch record called for the precipitation of the product in three portions in a 100-L reactor (~89 L each, Reactor A). The total reaction mixture volume to be quenched was ~64 L. The reaction mixture was transferred from Reactor A into two 50-L reactors covered with aluminum foil to exclude light. One third of the reaction mixture from Reactor A (~21 L) was transferred into a 50-L reactor (Reactor B) for the first precipitation and two thirds of the reaction mixture from Reactor A (~43 L) was transferred into another 50-L reactor (Reactor C) for the second and third precipitations.

Precipitation #1 and Filtration #1 Part A:

DI water (64.65 Kg) was weighed out into clean containers and pre-cooled in a refrigerator, then charged into Reactor A. The batch was cooled to 3.5° C. (target: 0-5° C.). The reaction mixture (~21 L) in Reactor B was slowly transferred into the cold water in Reactor A over 33 minutes while maintaining the batch temperature at 0-10° C. At the start of the precipitation, two liters of the reaction mixture were transferred and the flow was stopped and the quenched mixture was stirred for 5 minutes. Solid precipitation was observed immediately. The transfer was resumed and, after complete transfer, the quenched slurry was then stirred for 57 minutes at 5±5° C. The slurry was transferred into a filter funnel over 35 minutes. The batch was de-liquored for one hour.

Precipitation #2 and Filtration #1 Part 8:

DI water (64.65 Kg) was weighed out into clean containers and pre-cooled in a refrigerator, then charged into Reactor A. The batch was cooled to 3.5° C. (target: 0-5° C.). The reaction mixture (~21 L, ½ of volume from Reactor C) was slowly transferred into the cold water in Reactor A over 32 minutes while maintaining the batch temperature at 0-10° C. At the start of the precipitation, two liters of the reaction mixture were transferred and the flow was stopped and the quenched mixture was stirred for 5 minutes. Solid precipitation was observed immediately. The transfer was resumed and, after complete transfer, the quenched slurry was then stirred for 48 minutes at 5±5° C. The batch was smoothly transferred into the filter funnel on top of the wet cake in the filter funnel from the previous filtration. The combined solids in the filter funnel were de-liquored for 10 minutes. The wet cake in the filter funnel was then washed with water (4×32.3 Kg) and finally de-liquored for 2 hours and 3 minutes by applying vacuum to the filter funnel to afford 9.85 Kg of wet, crude 3a.

Precipitation #3 and Filtration #2:

DI water (64.65 Kg) was weighed out into clean containers and pre-cooled in a refrigerator, then charged into Reactor A. The batch was cooled to 4.0° C. (target: 0-5° C.). The reaction mixture (~21 L, remaining ½ of batch from Reactor C) was slowly transferred into the cold water in Reactor A over 35 minutes while maintaining the batch temperature at 0-10° C. At the start of the precipitation, two liters of the reaction mixture were transferred and the flow was stopped and the quenched mixture was stirred for 5 minutes. Solid precipitation was observed immediately. The transfer was resumed and, after complete transfer, the quenched slurry was then stirred for 42 minutes at 5±5° C. The batch was smoothly transferred into the filter funnel over 18 minutes. The batch was de-liquored for 12 minutes.

The wet cake in the filter funnel was washed with water (4×16.2 Kg) and finally de-liquored for 2 hours and 10 minutes by applying vacuum to the filter funnel to afford 5.90 Kg of wet, crude 3a.

Purification of Wet, Crude 3a (Re-Crystallization):

The combined wet, crude 3a (15.75 Kg) was transferred into Reactor B (50 L) followed by n-heptane (9.95 Kg) under nitrogen. The batch was heated to 35.1° C. and stirred for 6 minutes at ~36.0° C. to dissolve the solids. Between the two clear phases, a rag layer was observed and some insoluble materials were observed. The batch was filtered at 35-40° C. through an in-line filter (10 μm) to obtain clear solutions (biphasic) without a rag layer. The batch was settled for 14 minutes for phase separation. The bottom aqueous layer (~8.5 L) was removed. The batch (~20 L) was cooled from 38° C. to ~23° C. over one hour and 35 minutes. During the cooling, 3a crystallization occurred at 23.2° C. The batch temperature increased to 28.8° C. during crystallization due to the heat of crystallization and then decreased to 17.5° C. over 60 minutes (final jacket temperature 10° C.). The slurry was stirred for one hour at 10-20° C. and then cooled to −20.4° C. over 14 hours and then was stirred for 2 hours and 25 minutes at −20.4° C. The filtration was operated under a positive pressure nitrogen atmosphere.

The batch was transferred into a filter funnel over 13 minutes. After de-liquoring for 10 minutes under nitrogen, the filter cake was then washed with cold n-heptane (3.32 Kg, 0° C.) and then de-liquored for two hours and 4 minutes under a nitrogen atmosphere. The wet filter cake (8.33 Kg) was transferred into drying trays and dried under vacuum 50 Torr) at ambient temperature for one hour and 15 minutes and then at 20-30° C. over 88 hours to afford dried 3a (6.94 Kg, 81.3% yield). 3a analysis showed that 3a purity was 99.2% AUC by HPLC and water content was 0.006% (KF).

Preferred Process Parameters and Embodiments within Step 2—Preparation of 3/3a

Listed below are certain preferred process parameters for Step 2 in the synthese of the invention as shown in Schemes I, II and III above. Each preferred process parameter described for a particular step, such as this step, is a separate embodiment of the invention. The preferred process parameters in each step may be employed together with those of other steps such that each combination of preferred process parameters is also a separate embodiment of the invention. A synthesis according to the invention having one or more preferred process parameters in one or more steps is also a separate embodiment of the invention. Preferred process parameters for Step 2 include, but are not limited to:

Protect reaction mixture, product solution, and isolated product from light exposure to avoid photo-degradation (mitigates unwanted by-product formation);

A temperature range of 10°-30° C. (preferably 15°-20° C.) during addition of NaI into the reaction mixture (mitigates unwanted by-product formation);

Reaction temperature 20° to 30° C. (mitigates unwanted by-product formation);

A temperature range of 0° to 10° C. for a controlled aqueous quench of the reaction mixture into water and precipitation of 3/3a (mitigates unwanted by-product formation);

Dissolution temperature during recrystallization 30° to 40° C. (mitigates unwanted by-product formation);

Reactor Jacket temperature during recrystallization 50° C. (mitigates unwanted by-product formation);

Final isolation temperature −25° to −15° C. (high yield with controlled purity);

Drying temperature 20° to 30° C. (mitigates unwanted by-product formation);

3/3a Purity 98.0% HPLC (AUC);

A range of 2.0-3.0 (preferably 2.5) molar equivalents of NaI with respect to 2a input (less results in unwanted downstream impurities and more increases cost);

Acetone as the reaction solvent (mitigates unwanted by-product formation); and/or Recrystallization from n-Heptane at ~1/1 w/w with respect to 2/2a input wt. (high yield with controlled purity).

Example 3—Step 3

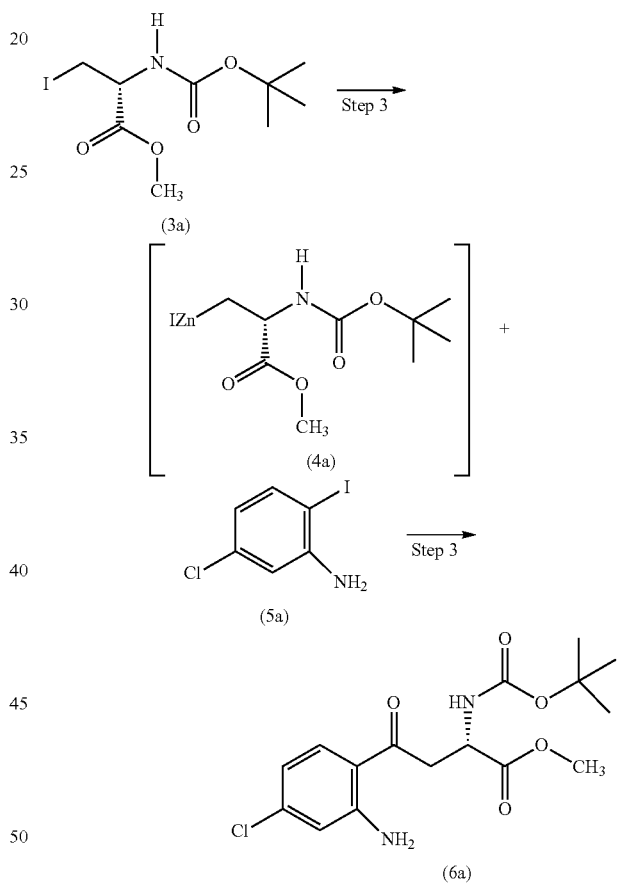

Example 3.1—Step 3: Lab Scale

A 500-mL round bottom flask was charged with zinc (0.54 mol), tetrahydrofuran (39 mL), and 1,2-dibromoethane (23 mmol) under an atmosphere of nitrogen. The reaction mixture was warmed to 60° C. and stirred for 5 minutes at 60° C. Then the reaction mixture was cooled to 30-35° C. and trimethylsilyl chloride (4.4 mmol) was charged to the flask. The reaction mixture was stirred at 30-35° C. for 30 minutes. After cooling the reaction to 20-25° C., the iodo intermediate (3a) (91 mmol) in tetrahydrofuran (180 mL) was charged to the flask over 1 h. The reaction mixture was stirred for 2 h at ambient temperature, at which point it was complete by thin layer chromatography (30% ethyl acetate in heptane, methanol quench, KMnO$_4$ stain, disappearance of 3a). A Porter-Fisher pressure bottle was charged with tetrakis(triphenylphosphine)-palladium(0) (4.6 mmol) and tetrahydrofuran (30 mL) under an atmosphere of nitrogen. Nitrogen was then bubbled into the solution and a vacuum was applied. Then carbon monoxide was bubbled into the solution and a vacuum was applied. The carbon monoxide was then bubbled into the reaction for 15 minutes with no vacuum. The Porter-Fisher pressure bottle was then charged with 5-chloro-2-iodoaniline (5a) (91 mmol) in tetrahydrofuran (25 mL). After the addition of the 5-chloro-2-iodoaniline (5a), the zinc reagent (4a) was transferred from the 500 mL round bottom flask to the Porter-Fisher pressure bottle over the course of 1 h, while maintaining carbon monoxide bubbling. Carbon monoxide was bubbled into the reaction for an additional 2 h with vigorous stirring. Then the bubbling apparatus was switched out for pressure fittings and the reaction was purged with carbon monoxide (6×15 psi) then left under carbon monoxide (3-4 psi) for 20 h. After placing the reaction back under an atmosphere of nitrogen, the reaction was filtered through a pad of celite (50% wt/wt) packed with ethyl acetate. The reaction vessel was rinsed with ethyl acetate (3×100 mL). Water (200 mL) and celite (20% wt/wt) were charged to the filtrate and stirred for 5 minutes. The mixture was filtered through a celite pad (50% wt/wt) and rinsed with ethyl acetate (150 mL). Filtrate was moved to a separatory funnel and a phase separation was performed. The lower aqueous layer was drained and discarded. Water (150 mL) was charged to the funnel and the solution was shaken for 3 minutes. A phase separation was performed and the lower aqueous layer was drained and discarded. The organic solvent was removed under reduced pressure to reveal crude intermediate 6a in quantitative yield.

Purification of Crude Intermediate 6a:

Crude intermediate (6a) was dissolved with 50 mL of ethyl acetate. The solution was loaded on a silica gel pad (300 g) and flashed with heptane (500 mL), 5% ethyl acetate/heptane (1.5 L), 10% ethyl acetate/heptane (1.0 L), 20% ethyl acetate (4.0 L). The product fractions were analyzed by HPLC and the fractions (purity higher than 80% AUC) were combined. After concentration of combined product solution, purified intermediate (6) (27.0 g, 83% yield, 95.2% AUC purity) was obtained.

Example 3.2—Step 3: Large Scale

Synthesis of 4a: (Non-Isolated Intermediate):

Zinc (7.74 kg, 5.9 equiv) was charged into a 50-L glass reactor (Reactor A) under nitrogen followed by THF (7.63 kg, 1.3 vol) and 1, 2-dibromoethane (0.941 kg, 0.25 equiv). The batch was stirred and heated from 16° C. to 61° C. over 1.5 hours (target: 60-65° C.). The batch was stirred for 7 minutes at 60-65° C. and then cooled to 36.8° C. over 65 minutes. Trimethylsilyl chloride (109 g, 0.05 equiv) was added over 13 minutes. The batch was stirred at 32-38° C. for 58 minutes and then cooled to 25.8° C. from 36.5° C. over 52 minutes. (3a) (6.60 kg, 1.0 equiv) was dissolved in a container with THF (29.3 kg, 5.0 vol) at ambient temperature. The (3a) solution was added into Reactor A (wrapped with aluminum foil to exclude light) over 2 hours and 10 minutes at 23±5° C. The batch was stirred for 2 hours and 20 minutes. TLC showed that (3a) had completely disappeared. Synthesis of (4a) was complete.

As part of the in-situ preparation of (4a), activation of zinc powder is required. While lab scale preparations proceed readily, manufacturing scale requires attention to mixing parameters in order to maintain suspension of the zinc powder. Settling of the zinc powder leads to incomplete activation and an incomplete reaction. Agitator settings are empirically determined for reactor/agitator type, geometry, and configuration.

Synthesis of (6a):

Tetrakis (tetrakis(triphenyphosphine)palladium(0), 1.161 kg, 0.05 equiv) was mixed with THF (total: 5.87 kg, using several rinses, 1.0 vol) in a container and the slurry was transferred into a 100-L glass reactor (Reactor B). Reactor B was purged 4 times with nitrogen (evacuating Reactor B using vacuum to a pressure of 200-250 Torr and then releasing the vacuum with nitrogen to atmospheric pressure). Reactor B was purged 4 times with carbon monoxide (CO) (evacuating Reactor B using vacuum to a pressure of 200-250 Torr and then releasing the vacuum with CO to atmospheric pressure). The batch was continuously purged with CO through sub-surface addition maintaining the CO flow in Reactor B at 4-6 LPM for 10 minutes. A pre-dissolved solution of (5a) (5.08 kg, 1.0 equiv) in THF (4.87 kg, 0.83 vol) was added into Reactor B over 9 minutes while maintaining the sub-surface CO flow at 4-6 LPM. The (4a) reaction mixture was transferred via a peristaltic pump from Reactor A into Reactor B over 61 minutes at 20-26° C. while maintaining the sub-surface CO flow at 4-6 LPM. Reactor A was rinsed with THF (1.76 kg) and the rinse was transferred into Reactor B. The batch was stirred at 20-26° C. while maintaining the CO pressure at 1-3 psig by bubbling CO sub-surface at a flow rate of 4-6 LPM for at least 20 hours. HPLC analysis after 20 hours showed that (6a) (vs. (5a)+ (6a)) reached 94.53% AUC. Adequate mass transfer of CO gas across the gas/liquid interface must be provided by a combination of surface area, gas pressure, and mixing. A second analysis 4 hours later showed that (6a) (vs. (5a)+ (6a)) increased 0.46% (to 94.99% AUC by HPLC) which was less that the targeted rate of increase specified to define reaction completion (≤1.0% HPLC AUC increase for (6a) over two consecutive samples at ≥4 hour intervals). The reaction was determined to be complete.

Reaction Work-Up:

After the reaction in Reactor b was complete, carbon monoxide bubbling was stopped and the system was evacuated using vacuum to a pressure of 200 Torr and then purged with nitrogen to atmospheric pressure. This purging process was repeated three times. The batch was then purged with nitrogen sub-surface at 4-6 LPM for 4 hours to reach a CO level in the head space of 35 ppm. The batch was settled for 15 minutes and the top liquid layer was decanted with a suction tube and filtered through a celite pad (4.7 kg, pre-wetted with ethyl acetate) over 43 minutes. Ethyl acetate (59.52 kg, 10 vol) was added into Reactor B to rinse the solids in Reactor B. The batch rinse was stirred for 15 minutes and settled for 20 minutes. The top layer was decanted with a suction tube and then transferred into the filter funnel for filtration. The filtrates (~120 L) were combined in a 55 gallon HDPE drum and water (39.6 kg, 6.0 vol) was added followed by celite (2.3 kg). The mixture in the drum was stirred with a drum stirrer for 15 minutes. Half of mixture was filtered through a celite pad (5.54 kg) pre-wetted with ethyl acetate into (cleaned) Reactor B. A very slow filtration was observed (~4 hours). The celite pad was washed with ethyl acetate (8.96 kg, 1.5 vol) and the rinse filtrate was transferred into Reactor B. The filtered mixture in Reactor B was stirred for 5 minutes and settled for 10 minutes. The bottom aqueous layer (~19 L) was removed and the top organic layer (~72 L) was washed with water (16.5 kg, 2.5 vol). The lower water layer was removed and the upper organic layer (~64 L) was transferred into a clean container. The second half of the drummed celite containing mixture was filtered via the used celite pad and the system was rinsed with ethyl acetate (8.93 kg, 1.5 vol). A very slow filtration and wash were observed (>3 hours). The filtered mixture was transferred into Reactor B and stirred for 6 minutes and settled for 8 hours. The bottom aqueous layer was removed and the top organic layer (~82 L) was washed with water (16.5 kg, 2.5 vol) and then the lower water layer was removed.

Isolation of Crude 6a:

The organic layer (~82 L) in Reactor B was vacuum concentrated to ~30 L in Reactor B and then the retained organic layer (~64 L) that had been stored in a clean container was transferred into Reactor B. The combined rich organic solution from Reactor B was concentrated to 4 Rota-vapor flasks to afford crude 6a (oily material, semi-solid, 11.98 kg in total). The crude isolated (6a) from the 4 Rota-vapor flasks was dissolved with ethyl acetate (~10 L) to afford a solution (20.25 kg) with some insoluble red solids present. The crude 6a mixture in ethyl acetate was then purified in 6 portions by silica gel purification.

Purification of Crude 6a on Silica Gel (Six Loadings):

The crude (6a) dissolved in ethyl acetate (~20 kg) was purified in 6 loadings on silica gel pads (Table 1). Each loading was calculated based on 1.1 kg of 3a input (6.6 kg in total). The silica gel weight with respect to (3a) input was 10 wt/wt. The silica pad was prepared from a slurry of silica gel in heptane. After applying the crude (6a) solution in a thin uniform layer, the purification was carried out by eluting with mixtures of ethyl acetate/heptane on a volume (v/v) basis (0%, 5%, 10%, 20% and 30% v/v ethyl acetate) using gravity flow and collecting the product fractions. After analysis, the combined relatively pure fractions (containing 6a 70% AUC by HPLC) for each loading were treated with activated carbon and filtered through a Celite pad. The filtrate was concentrated to afford purified 6a. The overall purification results are summarized in Table 1. Table 2 lists solvents used for each loading.

All of the purified (6a)/ethyl acetate solutions were combined to afford a single (6a)/ethyl acetate product solution (17.72 kg) which contained 5.88 kg of 6a (Total yield: 82.2%). HPLC analysis of this solution showed that HPLC purity was 95.68% AUC.

Example 3.3—Step-3: Preparation of 6a

Synthesis of 4a: (Non-Isolated Intermediate):

Reactor A (50-L glass reactor) was flushed with THF (~15 L) and the rinse was removed. The reactor then was rinsed with THF (~10 L) and the rinse was checked for water content. The water content was less than 0.1% confirming that the reactor was dry.

To remove zinc oxide from its surface, zinc powder was treated with a 50% w/w NaOH solution in water at a roughly 2:1 Zn:NaOH molar ratio with sufficient dilution to prevent the reaction of Zn metal with water to liberate hydrogen gas. The dried treated zinc (8.09 Kg, 5.9 equiv) was charged into Reactor A (50 L) under nitrogen followed by THF (8.00 Kg) and 1, 2-dibromoethane (0.984 g). The stirrer speed was set at 200 RPM. The batch was heated from 20.4° C. to 63.1° C. over 54 minutes (target: 63-65° C.). The batch was stirred for 10 minutes at 63-65° C. and then cooled to 33.1° C. over 68 minutes. Trimethylsilyl chloride (114.1 g) was added over 25 minutes while maintaining the batch temperature at 32-38° C. The batch was stirred at 32-38° C. for 60 minutes. The agitation was adjusted as needed to ensure thorough mixing of the zinc solids. The batch was cooled to 25.3° C. from 33.4° C. over 45 minutes. 3a (690 g, 10% of 3a for the batch: 6.90 Kg) was mixed with THF (3.07 Kg) in Reactor

TABLE 1

Purification Results for Crude 6a

| Loading | Crude (6a) (calculated) | Silica Gel | Silica Pad Thickness | Isolated (6a) | (6a) Purity (HPLC AUC) | Calculated Recovery |
|---|---|---|---|---|---|---|
| 1 | 3.39 Kg | 12.13 kg | ~12 cm | 910 g | 93.57% | 96.6% |
| 2 | 3.37 kg | 12.06 kg | ~12 cm | 1070 g | 93.78% | 95.2% |
| 3 | 3.38 kg | 12.08 kg | ~12 cm | 1020 g | 92.51% | 95.6% |
| 4 | 3.38 kg | 12.02 kg | ~12 cm | 1020 g | 93.27% | 97.1% |
| 5 | 3.37 kg | 12.01 kg | ~12 cm | 970 g | 92.78% | 97.1% |
| 6 | 3.18 kg [1] | 12.00 kg | ~12 cm | 890 g | 93.73% | 95.1% |
| Total Yield | | | | 5880 g 82.2%[2] | 95.68% | |

[1] Remainder in container.
[2] Yield based on final 6a oil/solid which may have contained residual solvent (EtOAc or heptane).

TABLE 2

Solvents Used for Silica Gel Purifications

| Loading (v/v) | 1 | 2 | 3 | 4 | 5 | 6 |
|---|---|---|---|---|---|---|
| Heptane | 11.30 kg | 11.32 kg | 11.32 kg | 11.30 kg | 11.33 kg | 11.31 kg |
| 5% EtOAc/heptane | 22.41 kg | 22.40 kg | 22.40 kg | 22.40 kg | 22.41 kg | 22.42 kg |
| 10% EtOAc/heptane | 11.41 kg | 11.44 kg | 11.41 kg | 11.41 kg | 11.40 kg | 11.40 kg |
| 20% EtOAc/heptane | 39.11 kg | 39.13 kg | 39.09 kg | 39.12 kg | 39.10 kg | 39.11 kg |
| 30% EtOAc/heptane | 24.40 kg | 24.40 kg | 24.50 kg | 24.40 kg | 24.40 kg | 24.40 kg |
| Additional 30% EtOAc/heptane | 24.45 kg | 24.41 kg | 24.41 kg | 24.40 kg | 24.41 kg | 24.40 kg |

B (50 L) at ambient temperature. The 3a mixture was adjusted to 22.5° C. (target: 20-26° C.) to afford a solution and then added into Reactor A (covered with aluminum foil to exclude light) over 40 minutes at 23-27° C. via a peristaltic pump. The batch was stirred for 30 minutes. TLC showed that 3a had completely disappeared. Initiation of 4a formation was complete.

The remaining 3a (6.90 Kg in total) was charged into Reactor B under nitrogen followed by THF (27.65 Kg). The mixture was adjusted from 15.2° C. to 20.8° C. and stirred for 10 minutes to obtain a solution. The solution was then added into Reactor A over three hours at 23-28° C. via a peristaltic pump. The batch was stirred for two hours. TLC showed that 3a had completely disappeared. 4a formation was complete.

Synthesis of 6a:

Pd(0)Tetrakis (1.21 Kg) was mixed with THF (total: 6.15 Kg) in a container and the slurry was transferred into a 100-L glass reactor (Reactor C). Reactor C was purged 4 times with nitrogen (evacuating the reactor to 200-250 Torr and then releasing the vacuum with nitrogen to atmospheric pressure). Reactor C was then purged 4 times with carbon monoxide (CO) (evacuating Reactor C to 200-250 Torr and then releasing the vacuum with CO to atmospheric pressure). The batch was then purged with CO maintaining the CO flow in Reactor C at 4-6 LPM for 10 minutes. A pre-dissolved solution of 5a (5.34 Kg) in THF (5.10 Kg) was added to Reactor C over 8 minutes via a peristaltic pump while maintaining the CO flow at 4-6 LPM. The 4a reaction mixture was transferred via a peristaltic pump from Reactor A into Reactor C over 2 hours at 20-26° C. Reactor A was rinsed with THF (1.84 Kg) and the rinse was transferred into Reactor C. The batch was stirred at 20-26° C. while maintaining CO pressure at 1-3 psig by bubbling CO at a flow rate of 4-6 LPM (through a 1 psig exhaust relief valve) for at least 20 hours. HPLC analysis after 20 hours showed that 6a (vs. 5a+6a) reached 85.04% AUC by HPLC. A second HPLC analysis after an additional 4 hours showed that 6a (vs. 5a+6a) increased 0.48% (to 85.52% AUC by HPLC) which met the criteria for reaction completion (less than 1% 6a AUC HPLC increase between consecutive samples).

6a Reaction Work-up:

After the reaction was complete, carbon monoxide bubbling was stopped and the system was evacuated using vacuum to the pressure 200-250 Torr and purging with nitrogen to atmospheric pressure. This purging process was repeated 4 times. The batch was bubbled with nitrogen for 50 minutes to reach CO in the head space at 35 ppm. The batch was settled for 65 minutes and the top liquid layer was transferred out and filtered through a Celite pad (5.0 Kg, pre-wetted with ethyl acetate) over 25 minutes. Ethyl acetate (62.25 Kg) was added into Reactor C to rinse the reactor. The batch was stirred for 25 minutes and settled for 19 minutes. The top layer was transferred into filter funnel for filtration. The filtrates (~120 L) were combined in a 55-G drum and water (41.40 Kg) was added followed by Celite (2.34 Kg). The mixture in the drum was stirred for 3 hours and 15 minutes. Half of mixture was filtered through a Celite pad (6.01 Kg) pre-wetted with ethyl acetate into Reactor C (previously cleaned). The celite pad was washed with ethyl acetate (9.35 Kg) and the filtrate was transferred into Reactor C. The mixture in Reactor C was stirred for 6 minutes and settled for 19 minutes. The bottom aqueous layer (~19 L) was removed and the top organic layer (~83 L) was washed with water (17.25 Kg). The obtained organic layer (~72 L) was transferred into a container. The second half of the slurried mixture was filtered via the used Celite pad and the system was rinsed with ethyl acetate (9.35 Kg). The mixture was transferred into Reactor C and stirred for 10 minutes and settled for 10 minutes. The bottom aqueous layer was removed and the top organic layer (~82 L) was washed with water (17.25 Kg).

Isolation of Crude 6a:

The organic layer (~79 L) in Reactor C was vacuum concentrated (≤50° C., ≤75 Torr) to 62 L and the obtained organic layer (~83 L) was further concentrated in 4 Rotavapor flasks to afford crude 6a (oily solids, 11.10 Kg in total). The crude 6a was dissolved with ethyl acetate (~9 L) to afford a solution (19.47 Kg). The crude 6a mixture was purified in 6 portions by silica gel plug purification.

Purification of Crude 6a:

The crude 6a dissolved in ethyl acetate (~9 L) was purified in 6 loadings on silica gel plugs. Each loading was calculated based on 1.15 Kg of 3a input (6.9 Kg in total). The silica gel loading to 3a input was 10.43× wt/wt. The silica pad was prepared with n-heptane. The 6a was eluted with ethyl acetate/n-heptane portions with increasing ethyl acetate content. Fractions were collected and analyzed by HPLC and the relatively pure fractions 85% HPLC AUC 6a) were combined. The combined relatively pure fractions from each loading were treated with activated carbon and filtered through a Celite pad. The filtrate was concentrated to afford purified 6a (5.57 Kg, 74.5% Yield, 95.63% HPLC AUC purity).

Preferred Process Parameters and Embodiments within Step 3-Preparation of 6/6a

Listed below are certain preferred process parameters for Step 3 in the synthese of the invention as shown in Schemes I, II and III above. The process conditions and parameters for Step 3 a high yielding carbonylation step using 4-chloro-2-X-aniline, (5) or 4-chloro-2-iodo-aniline (5a) in the carbonylation step with yields (~70-75%) exceeding published results for substituted aryl iodides (12-29% in Jackson et al., *JCS Perkin* 1, 1997, 865). These include robust conditions for large scale high yielding carbonylation to prepare 6a (which is also a novel compound per se). Each preferred process parameter described for a particular step, such as this step, is a separate embodiment of the invention. The preferred process parameters in each step may be employed together with those of other steps such that each combination of preferred process parameters is also a separate embodiment of the invention. A synthesis according to the invention having one or more preferred process parameters in one or more steps is also a separate embodiment of the invention. Preferred process parameters for Step 3 include, but are not limited to:

Reaction temperature range 23° to 27° C. (preferably ~25° C.) for the formation of the iodozinc intermediate 4/4a herein (aka 6/6a in Jackson et al., *JCS Perkin* 1, 1997, 865) from 3/3a and zinc powder (vs. 35° C. water bath in cited prior art reference) (provides suitable reaction kinetics while minimizing thermal decomposition);

Protection of the 4/4a reaction mixture from light to prevent photodegradation (mitigates undesired by-product formation);

Controlled addition of the 3/3a solution into the zinc powder slurry at a rate that maintains the reaction mixture at 23° to 27° C. (preferably ~25° C.) (provides suitable reaction kinetics while minimizing thermal decomposition);

Pre-saturation of the Pd(0)tetrakis catalyst slurry in THF with CO gas prior to the addition of 5/5a) into the reaction mixture (mitigates undesired by-product formation from homo-coupling of 5/5a);

Concurrent sub-surface addition of CO gas or CO gas pressure into the Pd(0)tetrakis/THF/5 or the Pd(0)tetrakis/THF/5a mixture during the addition of the 4/4a mixture (mitigates undesired by-product formation);

Addition of the 4 mixture into the Pd(0)tetrakis/THF/5 mixture or the 4a mixture into the Pd(0)tetrakis/THF/5a mixture at a controlled steady rate to achieve complete transfer in ≥60 minutes (preferably ~2 to 3 hours) (mitigates undesired by-product formation);

Protection of the 4/Pd(0)tetrakis/THF/5 reaction mixture or the 4a/Pd(0)tetrakis/THF/5a reaction mixture from light to prevent photodegradation (mitigates undesired by-product formation);

Reaction temperature of 20° to 26° C. for the carbonylation reaction (mitigates undesired by-product formation); and/or Continuous subsurface addition of CO gas or by CO gas pressure into the carbonylation reaction mixture at a rate providing a steady-state foam volume of ~2-8% (preferably ~4%) with respect to the total reaction mixture volume (mitigates undesired by-product formation).

Controlling the addition of CO gas or CO gas pressure provides a successful large-scale, high-yielding carbonylation from both the kinetics of CO dissolution into the reaction mixture and the dissolved CO concentration. As described in the preferred embodiment above, maintaining a controlled subsurface gas addition of CO provided a sufficient sustained dissolved CO concentration for a high yielding carbonylation at manufacturing scale. Alternatively, the use of a pressurized reaction vessel with gas entraining agitation can also provide effective CO gas mass transfer with sufficient sustained dissolved CO concentration for a high yielding carbonylation. A pressurized vessel may also result in dissolved CO concentrations that are too high, that is, high enough to inhibit the desired carbonylation reaction. Preferred CO pressures range from 1 psig to 100 psig. CO pressures of 1-5 psig preferred for operating in a continuous subsurface addition mode (mitigates undesired by-product formation). CO pressures of 20 to 100 psig preferred (with 80-100 psig most preferred) for operating in a closed pressurized reactor with continuously maintained CO pressurization (mitigates undesired by-product formation).

Example 4—Step 4

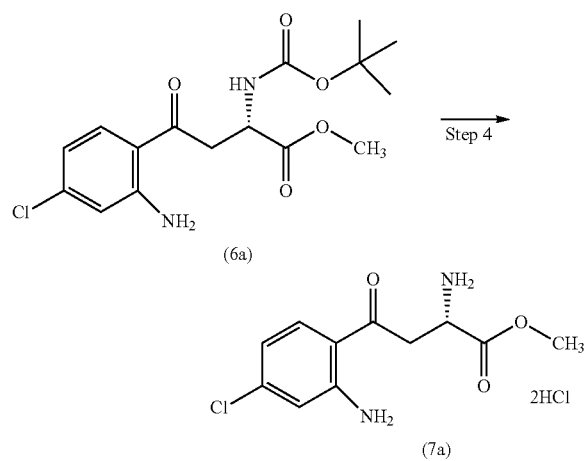

Example 4.1—Step 4: Lab Scale

A 500-mL 3-necked round bottom flask was charged with a solution of intermediate 6a (18 g, 50.45 mmol) in methyl acetate (180 mL) under nitrogen. The solution was cooled to 18° C. Then 4N HCl in dioxane (75 mL, 6 equiv.) was added dropwise over 45 minutes while maintaining the batch temperature at 18-25° C. The reaction was stirred and monitored by HPLC. The reaction was completed after 5.5 hours. The resulting slurry was filtered and the wet cake was washed with methyl acetate (2×10 mL) and dried under vacuum over night to afford methyl ester of L-4-chlorokynurenine di-HCl salt 7a (16.64 g, quantitative yield, 99.04% AUC purity).

Example 4.2—Step 4: Large Scale

7a Synthesis: BOC-Deprotection Reaction:

Ethyl acetate (39.55 kg, 10 vol in total) was charged into a 100-L glass Reactor (Reactor A) followed by DI water (288 g, 1 equiv). HCl solution (4N) in dioxane (29.59 kg, 7 equiv) was charged into Reactor A. The batch was adjusted to 20-30° C. 6a solution in ethyl acetate (total: 16.99 kg; 5.64 kg of 6a in 11.35 kg of ethyl acetate) was added into Reactor A via an in-line filter of 10 μm pore size at a uniform rate (100 mL/min) over three hours at 20-30° C. The 6a container and the transfer line were rinsed with ~3 L from the total required ethyl acetate and the rinse was transferred into Reactor A. Solids precipitated during the addition of the 6a solution. The batch was stirred for 16.5 hours under nitrogen and in the dark at 20-30° C. and a sample (uniform slurry sample) was submitted for a reaction conversion check. The results showed that the reaction was complete with 0.4% HPLC AUC of 6a remaining (target: 2.0% of 6a).

7a Isolation: Filtration and Washes:

The batch was filtered on a PE Buchner filter inside a 4-handed PE glove bag that had been purged with nitrogen for 15 minutes. The batch was transferred from Reactor A to the filter funnel via a peristaltic pump over one hour. The wet cake was deliquored for 15 minutes and washed with ethyl acetate twice. In the first wash ethyl acetate (10.2 kg) was charged into Reactor A to rinse the reactor and then transferred onto the filter cake. A second wash with ethyl acetate (10.2 kg) wash was performed in the same way.

The wet cake was dried in the filter funnel under nitrogen for 2 hours and 20 minutes by applying vacuum to the funnel and was then transferred into 6 glass drying trays (12.754 kg) using the glove bag to maintain a nitrogen atmosphere. The material was dried in a vacuum oven (≤50 Torr) for 15 hours and 30 minutes without heating and then dried at 20-30° C. (≤50 Torr) for 24 hours and 40 minutes to afford dried 7a (5.52 kg). The material was further dried for 4 hours and 35 minutes to 5.085 kg (LOD: 7.9%). The material was further dried for 66 hours and 45 minutes to 4.854 kg (LOD: 4.5%). The material was then dried for 4 hours and 5 minutes to afford 4.849 kg (LOD: 0.1%; passed the spec: ≤0.5%). The final dried material (4.82 kg, 92.5% yield) was discharged into a clean container lined with doubled cGMP certified low density polyethylene (LDPE) bags and purged with nitrogen prior to sealing. HPLC analysis showed that the purity was 96.37% AUC.

In the preparation of 7a process control avoids impurity formation. The order of addition in Example 4.1 was found to provide an unacceptable level of a process impurity. This was mitigated by changing the order of addition in example 4.2 and including water in the reaction mixture. The process must be operated under nitrogen protection to provide rigorous moisture exclusion especially for isolation of 7a and handling of the isolated solids which are extremely hygroscopic and deliquescent. 7a is very hygroscopic and also light sensitive and must be stored under nitrogen protected from light. The substrate solution (6a in ethyl acetate) was added into excess 4N HCl in dioxane. The 4N HCl/dioxane also deliberately contained added water (up to 1 molar equivalent with respect to 6a). Maintaining a large excess of acid with respect to substrate and having water present (to trap any t-butyl cations) mitigated the formation of an undesired t-butyl substituted by-product. Since 7a is very hygroscopic (and light sensitive), the product isolation was carried out under a nitrogen atmosphere. For this production, the filtration was performed in a nitrogen purged plastic glove bag. This configuration limited the wet cake deliquoring resulting in a higher than desired level of residual solvent in the filter cake and prolonged drying time.

Example 4.3—Step 4 Preparation of 7a

7a Synthesis: BOC-Deprotection Reaction:

Ethyl acetate (38.05 Kg) was charged into 100-L glass Reactor A followed by DI water (284 g). HCl solution (4N) in dioxane (28.70 Kg, 7.0 eq.) was charged into Reactor A. The batch was stirred and the temperature was adjusted to 20-30° C. 6a solution in ethyl acetate (total: 17.75 Kg; 5.57 Kg of 6a in 12.18 Kg of ethyl acetate) was added into Reactor A via an in-line filter of 10 μm pore size at a uniform rate (100 mL/min) over four hours and 46 minutes at 20-30° C. The 6a container and the transfer line were rinsed with ~3 L of ethyl acetate and the rinse was transferred into Reactor A. Solids precipitated during the addition of the 6a solution. The batch was stirred for 16 hours and 42 minutes under nitrogen and with exclusion of light at 20-30° C. and a sample (uniform slurry) was submitted to for reaction conversion confirmation. The results showed that the reaction was complete with 0.36% HPLC AUC of 6a remaining (target: 2.0% of 6a).

7a Isolation: Filtration and Washes:

The batch was filtered on a filter funnel inside a glove bag purged with nitrogen. The batch was transferred from Reactor A to the filter funnel via a peristaltic pump over 35 minutes and the wet cake was de-liquored for 30 minutes and then washed with ethyl acetate twice.

First wash: ethyl acetate (10.05 Kg) was charged into Reactor A to rinse the reactor and then transferred onto the filter cake. The wet cake was de-liquored for 10 minutes.

Second wash: ethyl acetate (10.05 Kg) was charged into Reactor A to rinse the reactor and then transferred onto the filter cake. The wet cake was de-liquored for 10 minutes.

The wet cake was dried in the filter funnel for 25 minutes by applying vacuum to the funnel under a positive nitrogen atmosphere and then transferred into glass drying trays. The material was dried in a vacuum oven 50 Torr) for one hour and 5 minutes without heating and then dried at 20-30° C. for 110 hours. The material (4.78 Kg, 92.85% yield) was discharged into a clean container lined with double API bags. HPLC analysis of the isolated 7a showed that the purity was 95.80% AUC.

Preferred Process Parameters and Embodiments within Step 4—Preparation of 7/7a

Step 4 involves deprotection and isolation of the de-protected intermediate as a dihydrochloride salt (7/7a) (7a is also a novel compound per se). Listed below are certain preferred process parameters for Step 4 in the synthese of the invention as shown in Schemes I, II and III above. Each preferred process parameter described for a particular step, such as this step, is a separate embodiment of the invention. The preferred process parameters in each step may be employed together with those of other steps such that each combination of preferred process parameters is also a separate embodiment of the invention. A synthesis according to the invention having one or more preferred process parameters in one or more steps is also a separate embodiment of the invention. Preferred process parameters for Step 4 include, but are not limited to:

Addition of 6/6a solution into HCl in 1,4-Dioxane (minimizes unwanted by-product formation);

Addition of 6/6a solution into HCl in 1,4-Dioxane at a controlled steady rate providing complete addition over 2-6 hours (preferably 4-6 hours) (minimizes unwanted by-product formation);

Reaction temperature of 20° to 30° C. (minimizes unwanted by-product formation);

Protection from light exposure to prevent photodegradation (minimizes unwanted by-product formation);

Protection of the isolated 7/7a from air/moisture exposure since the 7a is extremely hygroscopic and deliquescent (minimizes unwanted by-product formation);

Drying temperature 20° to 30° C. (minimizes unwanted by-product formation); and/or Yield of 7/7a≥95.0% HPLC (AUC).

Example 5—Step 5

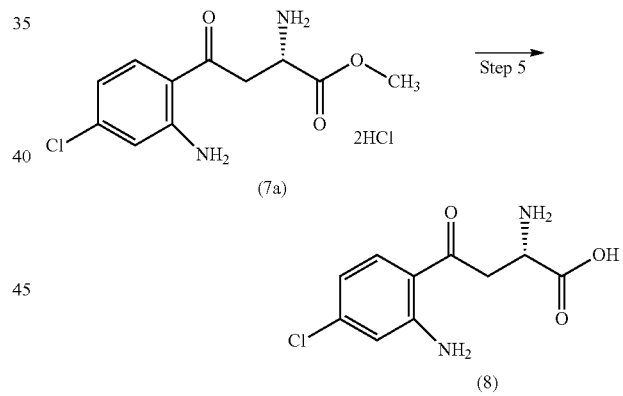

Example 5.1—Lab Scale Preparation of L-4-chlorokyurenine (8a)

A 250 mL round bottom flask was charged with methyl ester of L-4-chlorokynurenine di-HCl salt (7a) (4.04 g, 12.26 mmol) and water (10 mL). The reaction mixture was stirred for 10 minutes to a cloudy solution. 5.0N LiOH aqueous solution was added dropwise to the reaction mixture to pH (11-13) and the reaction was completed after 10-30 minutes. The reaction mixture was extracted with MIBK (50 mL). The aqueous layer was acidified by adding HCl (1N aqueous solution) to pH at 5-6. The slurry was stirred for 30 minutes and filtered. The wet cake was washed with water (2×10 mL) and dried under vacuum at 25-30° C. overnight to afford L-4-chlorokyurenine (8a) (2.81 g, 94.6% yield).

Example 5.2—Lab Scale Purification of
L-4-chlorokyurenine (8a)

L-4-chlorokyurenine (8a) (2 g) was mixed with 200 mL of methanol and then filtered. The filtrate was treated with active carbon (0.1 g) at ambient temperature for 10 minutes. The mixture was then filtered through a celite pad and washed with methanol (20 mL). The filtrate was concentrated to ~10 mL and then ethyl acetate (30 mL) was added. The slurry was stirred for 10 minutes and filtered to afford pure L-4-chlorokyurenine (8a) (0.8 g, 40% yield, 99.98% AUC purity).

Example 5.3—Large Scale Preparation of
L-4-chlorokyurenine (8a)

7a Free Base Solution Prep:

7a (4.76 kg, 1.0 equiv) was dissolved with water (47.61 kg, 10 vol) at 20-25° C. in a nitrogen purged 100-L reactor (Reactor A) which was covered with aluminum foil to protect the product from light. Some insoluble oily materials were observed. Toluene (32.9 kg, 10 vol) was added into the reactor. The reaction mixture was made alkaline from pH 0.83 (aqueous layer) to pH 8.45 (aqueous layer, target: pH 8.0-9.0) by adding concentrated $NH_4OH$ solution (28-30% wt/wt in water, 1.63 kg). The reaction mixture was stirred for 10 minutes at 20-25° C. to obtain a clear solution (biphasic solution). The reaction mixture was settled for 35 minutes to separate the phases. The bottom aqueous phase (~52 L) was transferred into a 50 L reactor (Reactor B) which was covered with aluminum foil to protect the product from light. The top organic layer (~42 L) was transferred into a 50-L reactor (Reactor C) which was covered with aluminum foil to exclude light. The aqueous solution from Reactor B was transferred back into Reactor A. Toluene (20.6 kg, 5 vol) was added into Reactor A. The reaction mixture in Reactor A was stirred for 13 minutes and the aqueous layer pH was 8.60 (target: pH 8.0-9.0). The mixture was settled for 17 minutes to allow phase separation. The bottom aqueous layer (~52 L) was transferred out into a container (for disposal). The top organic layer (~25 L) was held in Reactor A. The organic solution from Reactor C was transferred into Reactor for combination (total: 67 L). Water (9.53 kg, 2 vol) was added into Reactor A and the mixture was stirred for 12 minutes. The mixture in Reactor A was settled for 11 minutes for phase separation. The bottom aqueous layer (~10 L) was transferred into a container for disposal. A rich organic solution (7a free base solution, 67.5 L) was retained in Reactor A.

SiliaMetS Thiol Treatment of (7a) Free Base Solution—First Half—Part A:

A portion of the rich organic 7a Free Base solution (~34 L, 50% of the total solution) in Reactor A was transferred into Reactor C and Silia MetS Thiol from SiliCycle, Inc. (0.85 kg, 0.3 wt/wt, target: 0.71 kg) was added into Reactor C. Reactor C was covered with aluminum foil and the mixture was stirred for 15 hours at 20-25° C. An aliquot of the mixture (~10 mL) was taken and filtered using 0.45 urn syringe filter. The filtrate was concentrated to an oil (0.5470 g) which was submitted for Pd (limit <10 ppm) and Zn (limit <500 ppm) analysis. IPC results: Pd (1.0 ppm) and Zn (20 ppm). The reaction mixture was filtered through a celite pad (0.43 kg) in a Buchner funnel. The filtrate was transferred into Reactor B via an inline filter of 0.4 μm pore size. Toluene (2×2.06 kg, 2×0.5 vol) was used to rinse the Reactor C and then the celite filter pad forward into Reactor B.

Water (19.04 kg, 4 vol) was added into Reactor B and the mixture was stirred 20-25° C. The aqueous layer adjusted to pH 0.74 from pH 8.95 by adding 6N HCl solution (1.86 kg) at 20-25° C. The mixture was stirred for 10 minutes at 20-25° C. and then allowed phase separation to settle for 11 minutes. The bottom aqueous layer (22 L, 7a rich solution) was collected in a clean 55 gallon HDPE drum and held for later processing. The upper organic phase was held for further extraction.

SiliaMetS Thiol Treatment of 7a Free Base—Second Half—Part B:

The remaining rich organic 7a Free Base solution (~34 L, 50% of the total solution) in Reactor A was transferred into Reactor C and SiliaMetS Thiol (0.71 kg, 0.3 wt/wt) was added into Reactor C. Reactor C was covered with aluminum foil and the mixture was stirred for ca. 16.5 hours at 20-25° C. An aliquot of the mixture (~10 mL) was taken and filtered using 0.45 μm syringe filter. The filtrate was concentrated to an oil (0.5508 g) which was submitted for Pd (<10 ppm) and Zn (<500 ppm) analysis. IPC results: Pd (1.0 ppm) and Zn (1.0 ppm). The reaction mixture was filtered through a celite pad (0.45 kg) in a Buchner funnel. The filtrate was transferred into Reactor A via an inline filter of 0.4 μm pore size. Toluene (2×2.06 kg, 2×0.5 vol) was used to rinse the Reactor C and then the celite filter pad forward into Reactor A.

Water (19.04 kg, 4 vol) was added into Reactor A and the mixture was stirred at 20-25° C. The aqueous layer adjusted to pH 0.81 from pH 8.55 by adding 6N HCl solution (1.75 kg) at 20-25° C. The mixture was stirred for 10 minutes at 20-25° C. and then allowed phase separation to settle for 12 minutes. The bottom aqueous layer (23 L, (7a) rich solution) was collected in a clean 55 gallon HDPE drum together with the rich acidic 7a solution from part A.

The retained organic phase (~37 L, from Part A) in Reactor B was transferred into Reactor A and mixed with the organic phase from Part B. The combined organic solution (~73 L) was mixed with water (4.78 kg). The aqueous layer was adjusted to pH 0.62 from pH 3.96 by adding 6N HCl (0.25 kg). The mixture was stirred for 10 minutes at 20-25° C. and then allowed phase separation to settle for 10 minutes. The bottom aqueous layer (4 L, 7a rich solution) was transferred into Reactor B. The retained (7a) rich acidic solution from the 55 gallon HDPE drum (~45 L from Parts A & B) was transferred into Reactor B.

Hydrolysis of 7a:

The acidic 7a solution in Reactor B was cooled to 10.2° C. (5-15° C.). 4.5M lithium hydroxide solution (7.06 kg) was added into Reactor B at 10-20° C. over 31 minutes. The pH increased from pH 1.05 to pH 10.93. The reaction mixture pH was adjusted to and maintained at pH 12.0-12.5 at 10-20° C. by adding 4.5M H LiOH (2.19 kg). The reaction mixture was maintained at pH 12.0-12.5 at 10-20° C. for one hour and then a sample was submitted HPLC analysis. The results showed that the reaction was completed ((7a): 0.0% HPLC AUC remaining in the reaction mixture, Target: ≤0.5% AUC). The reaction mixture was quenched by slowly adding 6N HCl (2.53 kg) at 10-25° C. over 55 minutes over which time the pH was adjusted from pH 12.20 to pH 4.87 (target pH: 4.8-6.0). During the quenching, solid product started to precipitate at pH~9. The slurry at pH 4.8-6.0 was stirred for 65 minutes at 10-25° C. The slurry was filtered through a PE filter funnel over ~2.5 hours. The filtration was very slow. Reactor B was rinsed with water (2×9.54 kg, 2×2 vol) and the rinses were used to wash the filter cake. The filter cake wash was also very slow (at least two hours each).

The AV-101 wet cake in the filter funnel was deliquored for 13 hours by applying vacuum to the filter funnel.

Re-Precipitation of Crude, Semi-Purified 8a:

The wet cake (crude 8a, 21.09 kg) was transferred into Reactor A with water (23.83 kg, 5 vol) as a slurry to facilitate the transfer. The slurry in Reactor A was acidified to pH 0.65 from pH 5.02 at 10-25° C. by adding 6N HCl solution (3.46 kg). The mixture was stirred for 15 minutes to dissolve all solids (some lumps were slowly dissolved). The aqueous acidic solution in Reactor A was filtered through an in-line filter capsule (0.4 μm, pore size) over 45 minutes into Reactor B to remove any insoluble material. Concentrated ammonia hydroxide (0.82 kg) was added into Reactor B through an in-line filter capsule (0.4 μm, pore size). The reaction mixture pH increased from pH 0.65 to pH 1.77. Diluted $NH_4OH$ solution (10%, 3.5 kg) was added through an in-line filter capsule (0.4 μm, pore size) into Reactor B to adjust the pH to pH=5.15. The mixture was stirred for one hour at 10-25° C. while maintaining the pH at pH 4.8-6.0 by adding 6N HCl solution (~100 mL, as needed) through an in-line filter capsule (0.4 μm, pore size). The final slurry was filtered onto a PE filter funnel over 20 minutes. The wet cake was deliquored for 10 minutes. Water (2×7.14 kg, 2×2 vol) was transferred through an in-line filter capsule (0.4 μm, pore size) into Reactor B to rinse the reactor and the washes were transferred forward to rinse the filter cake. The final deliquoring required 25 minutes. The wet cake (10.669 kg, semi-purified 8a) was transferred into 6 drying trays and dried in a vacuum oven (≤50 Torr) for 40 hours without heating and then for 21 hours at 20-30° C. (≤50 Torr) to give 9.486 kg. The drying was continued at 20-30° C. for another 4 hours and the weight loss was 0.4% over the four hour time interval. Based on the final weight (9.486 kg) vs. the theoretical yield of 8a (3.50 kg) for this step, the semi-purified 8a contained 5.99 kg of water.

Example 5.4—Large Scale Purification of L-4-chlorokyurenine (8a)

The semi-purified 8a (9.38 kg) was transferred into Reactor B and mixed with methanol (11.29 kg, 3.0 vol) which was filtered through an in-line filter capsule (0.4 μm, pore size). Ethyl acetate (12.92 kg, 3.0 vol) was added into Reactor B through an in-line filter capsule (0.4 μm, pore size). The mixture was stirred for 18 hours and 20 minutes at 20-30° C. The slurry was filtered on a PE Buchner filter funnel over 45 minutes. The wet cake was deliquored for one hour and 45 minutes and then washed with methanol/ethyl acetate (1/1, v/v, 2.27 kg/2.58 kg, 1.2 vol) which had been pre-filtered through an in-line filter capsule (0.4 μm, pore size) and mixed in Reactor B. The wet cake was deliquored for one hour and then washed with filtered ethyl acetate (2×5.15 kg, 2×2.0 vol). The wet cake was deliquored for 50 minutes. A sample (~2 g, wet cake) was submitted purity (% AUC) analysis by HPLC. HPLC results showed that the purity was 99.80% AUC. All impurities were controlled to less than 0.1% HPLC AUC.

The wet cake (5.577 kg) was transferred into 6 glass drying trays and dried in a vacuum oven for one hour and 15 minutes (≤50 Torr) without heating and then for 52 hours with heating at 20-30° C. (heating set point at 28-30° C., ≤50 Torr) to provide 2.043 kg of dried material. The material was dried at 20-30° C. for another 16 hours which gave a final LOD=0.0%. A sample (1 g) was submitted for the residual solvent analysis. The GC results showed that all five residual solvents were below ICH Q3C Compliant specification limits for the process solvents, (methanol (MeOH), ethyl acetate (ETOAc), toluene, acetone and heptane).

Example 5.5—Step-5: Preparation of 8a

Preparation of 7a Free Base Solution and Residual Metal Mitigation:

7a as the di-HCl salt (4.77 Kg) was dissolved with water (47.66 Kg) at 20-25° C. in a 100-L reactor (Reactor A) covered with aluminum foil to protect the product from light exposure. Toluene (32.98 Kg) was added into the reactor. The reaction mixture was adjusted to pH 8.37 (target: pH 8.0-9.0) by adding concentrated $NH_4OH$ solution (28-30% wt/wt in water, 1.64 Kg). The reaction mixture was stirred for 15 minutes at 20-25° C. to give a clear (biphasic) solution. The reaction mixture was settled for 53 minutes to separate the phases. The lower aqueous phase (~52 L) was transferred into a 50 L reactor (Reactor B) covered with aluminum foil to protect the product from light. The top organic layer (~41 L) was transferred into a 50-L reactor (Reactor C). The aqueous solution from Reactor B was transferred back into Reactor A. Toluene (20.61 Kg) was added into Reactor A. The mixture in Reactor A was stirred for 13 minutes and the aqueous layer pH was 8.60 (target: pH 8.0-9.0). The mixture was settled for 10 minutes to allow phase separation. The bottom aqueous layer (~52 L) was transferred out into a container (for disposal). The organic solution from Reactor C was transferred into Reactor A and mixed (total: 65 L). Water (9.53 Kg) was added into Reactor A and the mixture was stirred for 22 minutes. The mixture in Reactor A was settled for 11 minutes for phase separation. The bottom aqueous layer (~12 L) was transferred into a container for disposal. A total of 65 L of 7a free base solution in toluene was obtained in Reactor A.

Metal Scavenger Treatment of 7a Free Base—First Half:

A portion of the rich organic solution (~33 L, ~50% total) from Reactor A was transferred into Reactor B and the metal scavenger, SiliaMetS Thiol®, (0.715 Kg) was added into Reactor B. Reactor B was covered with aluminum foil to exclude light and the mixture was stirred for 15 hours 22 minutes at 20-25° C. A sample was checked for residual metals by ICP/MS and showed: Pd (1.0 ppm) and Zn (20 ppm). The reaction mixture was filtered through a Celite pad (~0.5 Kg) in a filter funnel. The filtrate was transferred into Reactor C via an inline filter of 10 μm pore size. Toluene (2×2.06 Kg) was used to rinse Reactor B into the Celite filter pad and on into Reactor C.

Water (19.07 Kg) was added into Reactor C and the mixture was stirred 20-25° C. The aqueous layer was adjusted to pH 0.75 from pH 8.84 by adding 6N HCl solution (1.81 Kg) at 20-25° C. The mixture was stirred for 25 minutes at 20-25° C. and then allowed to settle for 28 minutes. The bottom aqueous layer (22 L, 7a rich solution) was collected in a clean 55-Gal HDPE drum.

Metal Scavenger Treatment of 7a Free Base—Second Half:

The remaining rich organic solution (~31 L, ~50% total) in Reactor A was transferred into Reactor B and the metal scavenger SiliaMetS Thiol® (0.72 Kg) was added into Reactor B. Reactor B was covered with aluminum foil to exclude light and the mixture was stirred for ca. 18.3 hours at 20-25° C. A sample was checked for residual metals by ICP/MS and showed: Pd (1.0 ppm) and Zn (10 ppm). The reaction mixture was filtered through a Celite pad (0.25 Kg) in a filter funnel. The filtrate was transferred into Reactor A via an inline filter of 10 µm pore size. Toluene (2×2.06 Kg) was used to rinse Reactor B into the Celite filter pad and on into Reactor A.

Water (19.07 Kg) was added into Reactor A and the mixture was stirred at 20-25° C. The aqueous layer adjusted from pH 9.03 to pH 0.74 by adding 6N HCl solution (1.74 Kg) at 20-25° C. The mixture was stirred for 19 minutes at 20-25° C. and then allowed to settle for 25 minutes. The bottom aqueous layer (23 L, 7a rich solution) was collected in a clean 55-Gal HDPE drum.

The organic solution (~35 L) in Reactor B was transferred into Reactor A and mixed. The combined organic solution (~73 L) was mixed with water (4.78 Kg). The aqueous layer was adjusted from pH 3.96 to pH 0.62 by adding 6N HCl (0.25 Kg). The mixture was stirred for 10 minutes at 20-25° C. and then allowed to settle for 10 minutes. The bottom aqueous layer (4 L, 7a rich solution) was transferred into Reactor B (previously cleaned). The 7a rich solution from the HDPE drum (~45 L) was transferred into Reactor B.

Hydrolysis of 7a and Isolation of Crude 8a:

The acidic aqueous solution of 7a in Reactor B was cooled to 10.5° C. (target: 5-15° C.). 4.5M lithium hydroxide solution (7.07 Kg) was added into Reactor B at 10-20° C. over 31 minutes. The pH went from pH 0.92 to pH 11.0 during the LiOH addition. The reaction mixture pH was adjusted to pH 12.0 to 12.5 at 10-20° C. by adding 4.5M H LiOH (2.48 Kg). The reaction mixture was maintained at pH 12.0 to 12.5 at 10-20° C. over one hour and 5 minutes and a sample was submitted for the determination of reaction completion. HPLC results showed that the reaction was completed (7a: non-detected, Target: ≤0.5% AUC). The reaction mixture was quenched by slowly adding 6N HCl (2.69 Kg) at 10-25° C. over 73 minutes. The pH was adjusted from pH 12.20 to pH 5.30 (target pH: 4.8-6.0). During the pH adjustment, solid product precipitated at pH~9. The final slurry at pH 4.8-6.0 was stirred for 65 minutes at 10-25° C. The slurry was filtered on a filter funnel. Reactor B was rinsed with water (2×9.50 Kg) and the rinse was transferred to the filter cake. The wet cake (8a) in the filter funnel was de-liquored for 15 minutes by applying vacuum to the filter funnel.

Re-Precipitation of Crude 8a (Purification #1):

The wet cake of crude 8a (11.50 Kg) was transferred into Reactor A followed by water (23.85 Kg). The slurry was acidified from pH 5.60 to pH 0.70 at 10-25° C. by adding 6N HCl solution (2.92 Kg). The mixture was stirred for 52 minutes to dissolve all solids. The aqueous acidic solution in Reactor A was filtered through an in-line filter capsule (0.4 µm, pore size) over 18 minutes into Reactor C. Concentrated ammonium hydroxide (0.82 Kg) was added into Reactor C through an in-line filter capsule (0.4 µm, pore size). The reaction mixture pH was increased from pH 0.70 to pH 1.95. Diluted NH₄OH solution (10% wt/wt, 2.16 Kg) was added through an in-line filter capsule (0.4 µm, pore size) into Reactor C to adjust the pH to pH 5.30. The mixture was stirred for one hour at 10-25° C. while maintaining pH at 4.8-6.0 by adding 6N HCl solution (as needed, ~105 mL) through an in-line filter capsule (0.4 µm, pore size). The slurry was filtered onto a filter funnel over 21 minutes. The wet cake was de-liquored for 11 minutes. Water (2×7.15 Kg) was transferred through an in-line filter capsule (0.4 µm, pore size) into Reactor C to rinse the reactor forward and to wash the filter cake. The final de-liquoring required 15 minutes. The wet cake of 8a (6.12 Kg) was transferred into drying trays and dried in vacuum oven for 15 hours and 17 minutes without heating and then 72 h at 20-30° C. to reach a final weight of 3.82 Kg.

Final Purification of 8a:

The dried 8a (3.82 Kg) was transferred into Reactor C and then mixed with methanol (11.31 Kg) filtered through an in-line filter capsule (0.4 µm, pore size). Ethyl acetate (12.92 Kg) was added into Reactor C through an in-line filter capsule (0.4 µm, pore size). The mixture was stirred for 22 hours and 30 minutes at 20-30° C. protected from light exposure. The slurry was filtered on a filter funnel. The wet cake was de-liquored for 13 minutes and then washed with methanol/ethyl acetate (1/1 v/v, 2.26 Kg/2.58 Kg) which was pre-filtered via an in-line filter capsule (0.4 µm, pore size) and mixed in Reactor C. The wet cake was de-liquored for 30 minutes and washed with filtered ethyl acetate (2×5.16 Kg). The wet cake was de-liquored for 60 minutes. The wet cake (3.99 Kg) was transferred into drying trays and dried in a vacuum oven. The materials were vacuum dried (~50 Torr) for 4 hours and 30 minutes without heating and then for 23 hours with heating at 20-30° C. (heating set point at 25° C.). The 8a solids were mechanically de-lumped and then transferred back to drying trays for continued drying. The materials were dried at 20-30° C. for 64 hours and 45 minutes to reach LOD=0.48% (LOD target: ≤0.5%). These operations successfully provided 8a (2.00 Kg, 99.36% HPLC AUC purity).

Preferred Process Parameters and Embodiments within Step 5—Preparation of 8

Step 5 involves the effective purge/control of residual metals and the ester hydrolysis, isolation and purification of L-4-chlorokynurenine (8a). Listed below are certain preferred process parameters for Step 5 in the synthese of the invention as shown in Schemes I, II and III above. Each preferred process parameter described for a particular step, such as this step, is a separate embodiment of the invention. The preferred process parameters in each step may be employed together with those of other steps such that each combination of preferred process parameters is also a separate embodiment of the invention. A synthesis according to the invention having one or more preferred process parameters in one or more steps is also a separate embodiment of the invention. Preferred process parameters for the residual metals mitigation in Step 5 include, but are not limited to:

Extraction of 7/7a from aqueous solution into toluene at pH=8.0-9.0 (provides phase partitioning of process impurities);

Protection of 7/7a solutions from light exposure (minimizes unwanted by-product formation); and/pr Treatment of 7/7a free base solution in toluene with SiliaMetS Thiol® (~20% w/w to 7/7a di-HCl input wt.) in order to control residual Zn to <500 ppm and residual Pd to <10 ppm (control of API quality).

Preferred process parameters for the the ester hydrolysis, isolation and purification of L-4-chlorokynurenine (8a) in Step 5 include, but are not limited to:

Protection of 7/7a solutions from light exposure to prevent photodegradation (minimizes unwanted by-product formation);

Extraction of 7/7a free base from toluene solution into aqueous acid at pH=0.5-0.9 preferably with aqueous HCl solution (minimizes unwanted by-product formation);

Hydrolysis of 7/7a in aqueous alkaline conditions using LiOH solution to achieve pH=12.0-12.5 (minimizes unwanted by-product formation);

Hydrolysis of 7/7a to form 8a at pH=12.0-12.5 (minimizes unwanted by-product formation);

Hydrolysis of 7/7a to form 8a at pH 12.0-12.5 in a temperature range of 10°-20° C. protected from light exposure to prevent photodegradation (minimizes unwanted by-product formation);

Isolation of 8a by controlled pH adjustment to pH=4.8-6.0;

Isolation of 8a by controlled pH adjustment with aqueous HCl to pH=4.8-6.0;

Purification of 8a by dissolution in aqueous acid at pH=0.5-0.9, then pH controlled precipitation by adjusting to pH=4.8-6.0 with aq. ammonia;

Drying of the water wet 8a at 20° to 30° C. (minimizes unwanted by-product formation);

Final purification of 8a by trituration in methanol/ethyl acetate 1/1 v/v; and/or Final drying of 8a at 20° to 30° C. (minimizes unwanted by-product formation).

The claimed invention is:

1. A method for the enantio-specific preparation of 4-chlorokynurenine (8) according to Scheme I,

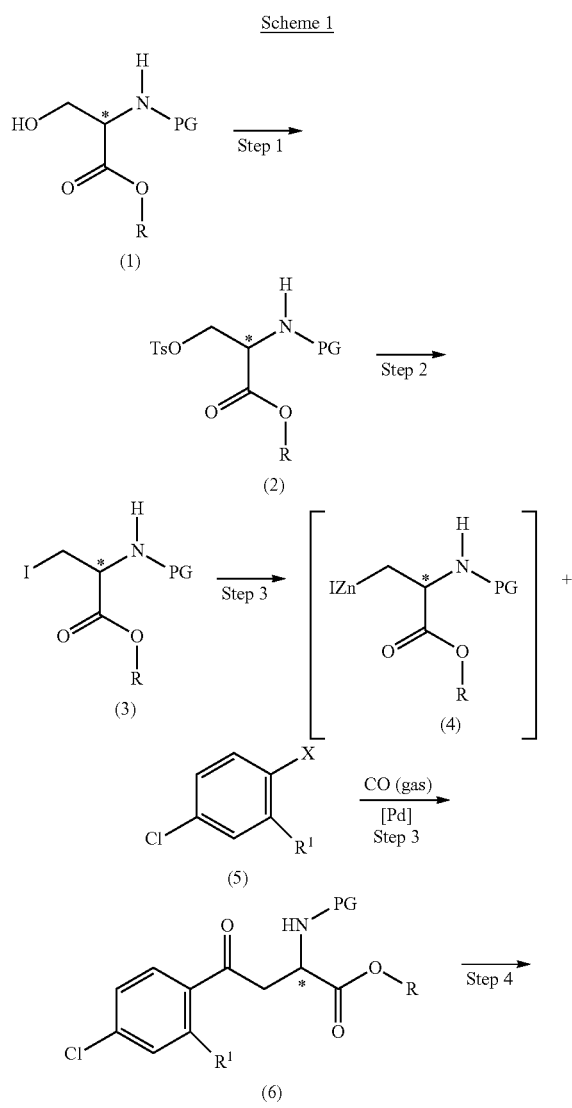

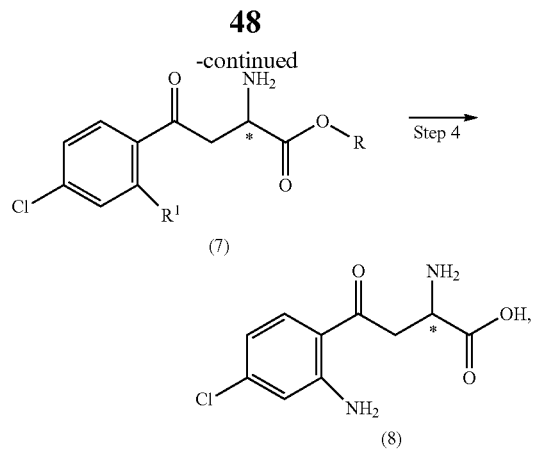

wherein
R is a $C_1$-$C_{12}$ alkyl group, a $C_1$-$C_{12}$ alk-aryl group, an aryl group, or a heteroaryl group;
* indicates an asymmetric carbon which may be a single enantiomer or a mixtures of enantiomers which is maintained throughout;
PG is an amino protecting group;
Ts is a tosyl group;
$R^1$ is $NH_2$, NH(PG) or $NO_2$; and
X is Cl, Br, I, triflate or tosylate; and
comprising the steps of:

Step 1, reacting a protected serine ester (1) with toluenesulfonyl chloride under suitable reaction conditions to convert the protected serine ester to its corresponding tosylate (2), Step 2, reacting the tosylate (2) with sodium iodide or potassium iodide under an inert atmosphere in the absence of light under suitable reaction conditions to replace the tosyl group with iodide and form the corresponding iodo intermediate (3), Step 3, converting the iodo intermediate (3) in situ to a zinc reagent (4) in the absence of light under suitable reaction conditions and forming a protected ester compound (6) via a carbonylation reaction reacting the zinc reagent (4) with a compound (5) in the presence of a palladium (0) catalyst [Pd] under suitable reaction conditions and while maintaining a sustained dissolved CO concentration either by continuous subsurface CO addition and/or CO pressure, optionally purifying the protected ester compound (6), and Step 4, deprotecting the protected ester compound (6) in the absence of light under suitable reaction conditions to remove any protecting group PG, and, when $R^1$ is $NO_2$, reducing the $NO_2$ group to an $NH_2$ group, to form the ester (7), deprotecting the ester (7) in the absence of light without exposure to air under suitable basic reaction conditions and adjusting the pH to an acidic pH to form 4-chlorokynurenine (8), wherein the deprotection of protected ester compound (6), the deprotection of ester (7), and the reduction of the $NO_2$ group to an $NH_2$ group are done in a single step or in multiple steps.

2. A method of claim 1, further comprising at least one of the following:
in Step 1, the presence of a catalytic amount of 4-dimethylaminopyridine and, optionally isolating and recrystallizing the tosylate (2);
in Step 2, an aqueous quench of the reaction mixture into water to precipitate the iodo intermediate (3) and, optionally, recrystallization of the iodo intermediate (3);

in Step 3, the palladium (0) catalyst [Pd] is Pd(0) tetrakis and with a CO pressure ranging from 1 psig to 1,000 psig; and in Step 4, deprotecting the protected ester compound (6) to remove any protecting group PG using HCl in dioxane and isolating the ester (7) in the absence of light without exposure to air or moisture and, in a separate deprotection step, hydrolyzing (7) at a pH of 12.0 to 12.5 and adjusting the pH to an acidic pH to form 4-chlorokynurenine (8).

3. A method of claim 1, wherein in Step 4 adjusting the pH to an acidic pH to form 4-chlorokynurenine (8) comprises the steps of:

isolating the 4-chlorokynurenine (8) from the alkaline solution as a free acid by pH adjustment of the alkaline solution with an aqueous acid to a pH below 6.5, dissolving the isolated free acid (8) in aqueous acid at a pH below 2, precipitating the free acid (8) by adjusting the pH of the aqueous acid solution of (8) to 4.5 to 6.5, collecting the precipitated free acid (8), drying the collected free acid (8), and optionally, triturating the collected free acid (8) using an organic solvent or an organic solvent mixture and drying the triturated free acid (8).

4. A method of claim 1, wherein

R is a $C_1$-$C_6$ alkyl group;

PG is an amine protecting group selected from BOC, Fmoc, benzyl, benzoyl, alkylamine, arylamine, TFA, and CBz; and X is I.

5. A method of claim 4, wherein

R is a methyl group,

PG is the amino protecting group BOC, and

X is I.

6. A method for the preparation of L-4-chlorokynurenine (8a) according to Scheme

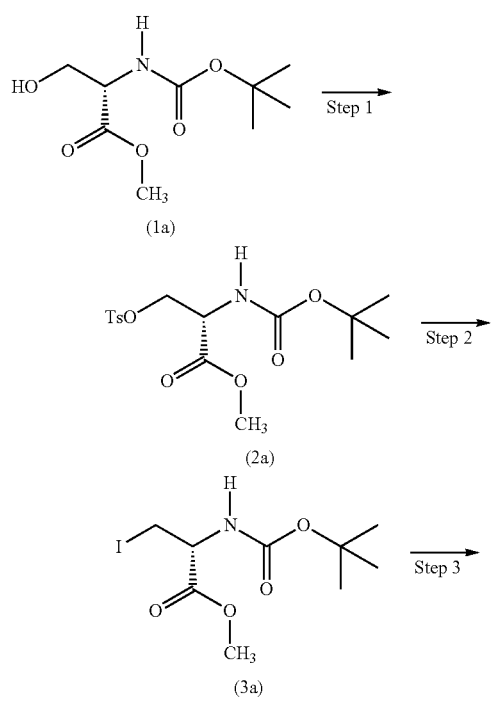

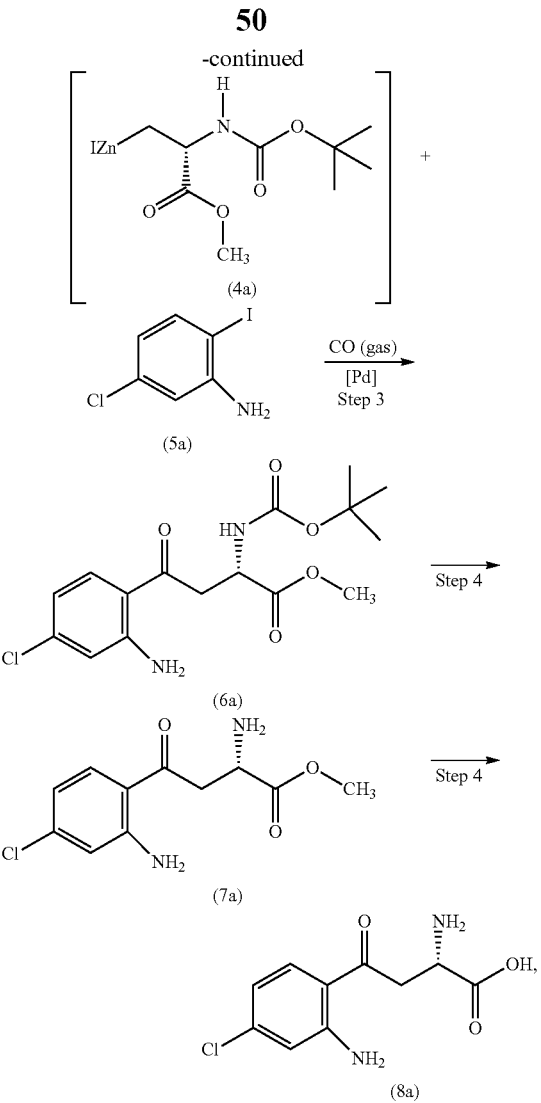

Scheme II, wherein Ts is a tosyl group and comprising the steps of:

Step 1, reacting a BOC-L-serine methyl ester (1a) with 1 to 2 molar equivalents of toluenesulfonyl chloride under suitable reaction conditions to convert the BOC-L-serine methyl ester (1a) to its corresponding tosylate (2a), Step 2, reacting the tosylate (2a) with sodium iodide or potassium iodide under an inert atmosphere in the absence of light under suitable reaction conditions to replace the tosyl group with iodide and form the corresponding iodo intermediate (3a), Step 3, converting the iodo intermediate (3a) in situ to a zinc reagent (4a) in the absence of light under suitable reaction conditions and forming a BOC-protected methyl ester compound (6a) via a carbonylation reaction reacting the zinc reagent (4a) with a 5-chloro-iodo aniline compound (5a) in the presence of a palladium (0) catalyst [Pd] and while maintaining a sustained dissolved CO concentration either by continuous subsurface CO addition and/or CO pressure, optionally purifying the protected ester compound (6a), and Step 4, deprotecting the BOC protected ester compound (6a) in the absence of light under suitable reaction conditions to remove the protecting group to form the methyl ester (7a), then deprotecting the methyl ester (7a) in the absence of light without exposure to air under suitable basic reaction conditions and adjusting the pH to an acidic pH to form 4-chlorokynurenine (8a), wherein the deprotection of protected ester compound (6a), and the deprotection of ester (7a) are done in a single step or in two steps.

7. A method of claim 6, further comprising at least one of the following:
   in Step 1, the presence of a catalytic amount of 4-dimethylaminopyridine and, optionally isolating and recrystallizing the tosylate (2a);
   in Step 2, an aqueous quench of the reaction mixture into water to precipitate the iodo intermediate (3a) and, optionally, recrystallization of the iodo intermediate (3a);
   in Step 3, the palladium (0) catalyst [Pd] is Pd(0) tetrakis with a CO pressure ranging from 1 psig to 1,000 psig; and
   in Step 4, deprotecting the BOC protected ester compound (6a) using HCl in dioxane and isolating the methyl ester (7a) in the absence of light without exposure of the isolated solids to air or moisture and, in a separate deprotection step, hydrolyzing (7a) with an aqueous base selected from NaOH, KOH, and LiOH.

8. A method of claim 6, wherein in Step 4 adjusting the pH to an acidic pH to form L-4-chlorokynurenine (8) comprises the steps of:
   isolating the L-4-chlorokynurenine (8a) from the alkaline solution as a free acid by pH adjustment of the alkaline solution with an aqueous acid to a pH below 6.5,
   dissolving the isolated free acid (8a) in aqueous acid at a pH below 2,
   precipitating the free acid (8a) by adjusting the pH of the aqueous acid solution of (8a) to 4.5 to 6.5
   collecting the precipitated free acid (8a),
   drying the collected free acid (8a), and
   optionally, triturating the collected free acid (8a) using an organic solvent or an organic solvent mixture and drying the triturated free acid (8a).

9. A method for the preparation of L-4-chlorokynurenine (8a) from a compound (6a)

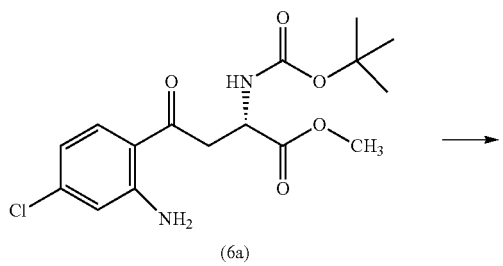

(6a)

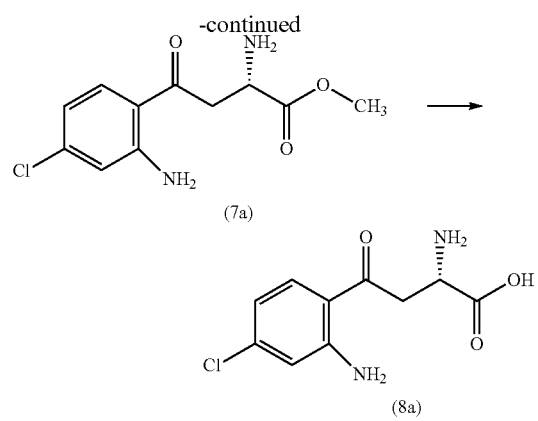

(7a)

(8a)

comprising the steps of:
   deprotecting the BOC protected ester compound (6a) in the absence of light under suitable reaction conditions to remove the protecting group to form the methyl ester (7a), then deprotecting the methyl ester (7a) in the absence of light without exposure to air under suitable basic reaction conditions and adjusting the pH to an acidic pH to form 4-chlorokynurenine (8a), wherein the deprotection of protected ester compound (6a), and the deprotection of ester (7a) are done in a single step or in two steps.

10. A method of claim 9, wherein the deprotection steps comprise
   deprotecting the BOC protected ester compound (6a) using HCl in dioxane and isolating the methyl ester (7a) in the absence of light without exposure of the isolated solids to air or moisture and, in a separate deprotection step, hydrolyzing (7a) with an aqueous base selected from LiOH, NaOH, and KOH, at a pH of 12.0 to 12.5 and adjusting the pH to an acidic pH to form L-4-chlorokynurenine (8a).

11. A method of claim 9, wherein in adjusting the pH to an acidic pH to form L-4-chlorokynurenine (8a) comprises the steps of:
   isolating the free acid (8a) from the alkaline solution by pH adjustment of the alkaline solution with an aqueous HCl to a pH of 4.8 to 6.0,
   dissolving the isolated free acid (8a) in aqueous acid at a pH of 0.5 to 0.9,
   precipitating the free acid (8a) by adjusting the by pH of the aqueous acid solution of (8a) to a pH of 4.8 to 6.0,
   collecting the precipitated free acid (8a), and
   drying the collected free acid (8a).

12. A method of claim 6, wherein the L-4-chlorokynurenine (8a) prepared has a chiral purity of ≤0.5% of D-4-chlorokynurenine.

* * * * *